United States Patent [19]

Buzzetti et al.

[11] Patent Number: 5,656,654
[45] Date of Patent: Aug. 12, 1997

[54] ARYLIDENE AND HETEROARYLIDENE OXINDOLE DERIVATIVES AND PROCESS FOR THEIR PREPARATION

[75] Inventors: Franco Buzzetti, Monza; Antonio Longo, Milan; Maria Gabriella Brasca, Cusago; Fabrizio Orzi, Milan; Angelo Crugnola, Varese; Dario Ballinari, San Donati Milanese; Mariangela Mariani, Desio, all of Italy

[73] Assignee: Farmitalia Carlo Erba S.r.l., Milan, Italy

[21] Appl. No.: 263,666

[22] Filed: Jun. 22, 1994

[30] Foreign Application Priority Data

Jul. 1, 1993 [GB] United Kingdom ............ 9313638

[51] Int. Cl.$^6$ .............. C07D 209/34; C07D 401/04; A61K 31/40; A61K 31/47
[52] U.S. Cl. .............. 514/412; 514/307; 514/314; 546/144; 546/165; 548/475
[58] Field of Search .............. 514/412, 307, 514/314; 546/144, 165; 548/475

[56] References Cited

U.S. PATENT DOCUMENTS

| 5,122,537 | 6/1992 | Buzzetti et al. |
| 5,130,472 | 7/1992 | Buzzetti et al. |

FOREIGN PATENT DOCUMENTS

| 0 525 472 | 2/1993 | European Pat. Off. |
| 0 549 348 | 6/1993 | European Pat. Off. |
| WO91/13055 | 9/1991 | WIPO |
| WO92/07830 | 5/1992 | WIPO |
| WO93/01182 | 1/1993 | WIPO |

*Primary Examiner*—Jacqueline Haley
*Attorney, Agent, or Firm*—Oblon, Spivak, McClelland, Maier & Neustadt, P.C.

[57] ABSTRACT

Arylidene and heteroarylidene oxindole derivatives of formula (I)

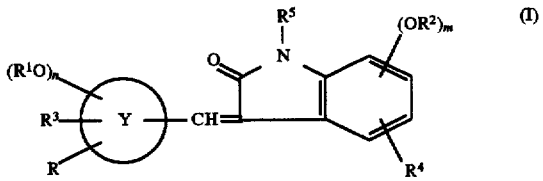

wherein, subject to provisos,

Y is a bicyclic ring system chosen from naphthalene, tetralin, quinoline and isoquinoline;

R is hydrogen or an oxo (=O) group when Y is tetralin; or

R is hydrogen when Y is naphthalene, quinoline or isoquinoline;

each of $R^1$ and $R^2$ independently is hydrogen, $C_1$–$C_6$ alkyl or $C_2$–$C_6$ alkanoyl;

m is zero, 1 or 2;

n is zero, 1, 2 or 3;

each of $R^3$ and $R^4$ independently is hydrogen, halogen, cyano, $C_1$–$C_6$ alkyl, carboxy, nitro or —$NR^6R^7$ in which each of $R^6$ and $R^7$ independently is hydrogen or $C_1$–$C_6$ alkyl;

$R^5$ is hydrogen or $C_1$–$C_6$ alkyl; and their pharmaceutically acceptable salts, which are useful as tyrosine kinase inhibitors.

18 Claims, No Drawings

ARYLIDENE AND HETEROARYLIDENE OXINDOLE DERIVATIVES AND PROCESS FOR THEIR PREPARATION

The present invention relates to new 3-arylidene and 3-heteroarylidene-2-oxindole derivatives, to a process for their preparation, to pharmaceutical compositions containing them and to their use as therapeutic agents. The present invention provides compounds having the following general formula (I)

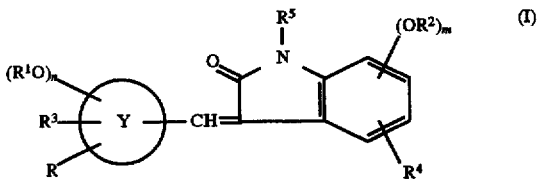

wherein

Y is a bicyclic ring system chosen from naphthalene, tetralin, quinoline and isoquinoline;

R is hydrogen or an oxo (=O) group when Y is tetralin, or R is hydrogen when Y is naphthalene, quinoline or isoquinoline;

each of $R^1$ and $R^2$ independently is hydrogen, $C_1$–$C_6$ alkyl or $C_2$–$C_6$ alkanoyl;

m is zero, 1 or 2;

n is zero, 1, 2 or 3;

each of $R^3$ and $R^4$ independently is hydrogen, halogen, cyano, $C_1$–$C_6$ alkyl, carboxy, nitro or —$NR^6R^7$ in which each of $R^6$ and $R^7$ independently is hydrogen or $C_1$–$C_6$ alkyl;

$R^5$ is hydrogen or $C_1$–$C_6$ alkyl; and the pharmaceutically acceptable salts thereof; and wherein a) when at the same time Y is naphthalene; $R^3$ is hydrogen, halogen, cyano or $C_1$–$C_6$ alkyl; $R^5$ is hydrogen; m is zero and n, R and $R^1$ are as defined above, then $R^4$ is other than hydrogen;

b) when at the same time Y is quinoline or isoquinoline; $R_3$ is hydrogen, halogen, cyano or $C_1$–$C_6$ alkyl; n is zero, 1 or 2; $R^5$ is hydrogen; m is zero and R and $R^1$ are as defined above, then $R^4$ is other than hydrogen;

c) when at the same time Y is tetralin in which only the benzene moiety is substituted, $R^3$ is hydrogen, halogen, cyano or $C_1$–$C_6$ alkyl; n is zero, 1 or 2; $R^5$ is hydrogen; m is zero, R is hydrogen and $R^1$ is as defined above, then $R^4$ is other than hydrogen; and d) when at the same time Y is naphthalene; m and n are zero; R and $R^3$ are hydrogen; $R^4$ being linked at the C-4 carbon atom is halogen or $C_1$–$C_4$ alkyl, then $R^5$ is other than $C_1$–$C_2$ alkyl.

The invention includes within its scope all the possible isomers, stereoisomers, in particular Z and E isomers and their mixtures, and the metabolites and the metabolic precursors or bio-precursors (otherwise known as pro-drugs) of the compounds of formula (I).

The alkyl group, and the alkyl moiety in the alkanoyl groups, may be branched or straight alkyl chain. A $C_1$–$C_6$ alkyl group is preferably a $C_1$–$C_4$ alkyl group, e.g. methyl, ethyl, propyl, isopropyl, butyl, sec-butyl or tert-butyl, in particular methyl or ethyl. A $C_2$–$C_6$ alkanoyl group is preferably a $C_2$–$C_4$ alkanoyl group, in particular acetyl, propionyl or butyryl.

A halogen is preferably fluorine, chlorine or bromine, in particular fluorine or chlorine.

The term tetralin preferably is meant to refer to a 5,6,7,8-tetrahydronaphthalene ring system.

When the R oxo (=O) group is a substituent on the tetralin ring, said oxo group can be attached only to the saturated moiety of the tetralin ring, thus providing a 5-, 6-, 7- or 8-tetralone ring system, preferably 8-tetralone.

When Y is tetralin preferably the oxindolylidene substituent is on the benzene moiety whereas the $R^3$ and the $R^1O$-group(s) may be on either of the rings.

When tetralin is substituted at the position 1' by the oxindolylidene substituent, preferably at least one —$OR^1$ group is present at the positions 2', 4', 5' and/or 8' and preferably the $R^3$ substituent is at the 4' position.

Analogously when tetralin is substituted at the 2'-position by the oxindolylidene substituent, preferably at least one —$OR^1$ group is present at the positions 1', 3', 4', 5' and/or 8' and the $R^3$ substituent is preferably at the 4'-position.

When Y is naphthalene the $R^3$, the $R^1O$-group(s) and the oxindolylidene substituents are preferably on the same benzene moiety.

When Y is quinoline the oxindolylidene group is preferably attached to the 4'- or 5'-position of the quinoline ring whereas the $R^3$ and $R^1O$ substituents may be on either of the rings of said ring system.

When Y is isoquinoline the oxindolylidene group is preferably attached to the 3'- or 5'-position of the isoquinoline ring whereas the $R^3$ and $R^1O$ substituent(s) may be on either of ring moieties.

When Y is quinoline, it is preferably substituted at the positions 4' or 5' by the oxindolylidene substituent and at least one OR' substituent is present, preferably at the 8' position.

Preferably at least one of the substituents $R^4$ or —$OR^2$ is present on the 2-oxindole ring. Preferred substitution positions are the positions 4 and 5, in particular position 5.

When $R^4$ is carboxy, nitro or —$NR^6R^7$ in which $R^6$ and $R^7$ are as defined above, the $R^3$ substituent is preferably other than carboxy, nitro or —$NR^6R^7$. Vice versa, when $R^3$ is carboxy, nitro or —$NR^6R^7$ in which $R^6$ and $R^7$ are as defined above, the $R^4$ substituent preferably is other than carboxy, nitro or —$NR^6R^7$.

Of course only one of the substituents $R^1O$, $R^2O$, $R^3$, R and $R^4$ can be linked to the same ring position.

Pharmaceutically acceptable salts of the compounds of the invention include acid addition salts, with inorganic, e.g. nitric, hydrochloric, hydrobromic, sulphuric, perchloric and phosphoric acids, or organic, e.g. acetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium, bases or alkaline-earth metal, especially calcium or magnesium bases, or with organic bases, e.g. alkylamines, preferably triethylamine.

As stated above, the present invention also includes within its scope pharmaceutically acceptable bioprecursors (otherwise known as pro-drugs) of the compounds of formula (I), i.e. compounds which have a different formula to formula (I) above, but which nevertheless upon administration to human being are converted directly or indirectly in vivo into a compound of formula (I).

Preferred compounds of the invention are the compounds of formula (I), wherein subject to the above provisos, Y is tetralin, quinoline or isoquinoline;

n is zero, 1, 2 or 3;

m is zero or 1;

each of $R^1$ and $R^2$ independently is hydrogen or $C_1$–$C_4$ alkyl;

each of $R^3$ and $R^4$ independently is hydrogen, halogen, cyano, carboxy or amino;

$R^5$ is hydrogen;

R is defined above; and the pharmaceutically acceptable salts thereof.

More preferred compounds of the invention are the compounds of formula (I), wherein subject to the above provisos, Y is tetralin or quinoline;
n is zero, 1, 2 or 3;
m is zero or 1;
$R^1$, $R^2$ and $R^5$ are hydrogen;
each of $R^3$ and $R^4$ independently is hydrogen, amino or carboxy;

R is as defined above; and the pharmaceutically acceptable salts thereof.

Examples of specific compounds of the invention are the following compounds, which, when appropriate, may be either Z- or E-diastereoisomers or Z, E-mixtures of said diastereoisomers.

3-[(4'-amino-1'-tetralyl)methylene]-2-oxindole;
3-[(4'-dimethylamino-1'-tetralyl)methylene]-2-oxindole;
3-[(4'-carboxy-1'-tetralyl)methylene]-2-oxindole;
5-hydroxy-3-[(1'-tetralyl)methylene]-2-oxindole;
5-amino-3-[(1'-tetralyl)methylene]-2-oxindole;
5-carboxy-3-[(1'-tetralyl)methylene]-2-oxindole;
5-hydroxy-3-[(2'-hydroxy-1'-tetralyl)methylene]-2-oxindole;
5-hydroxy-3-[(4'-hydroxy-1'-tetralyl)methylene]-2-oxindole;
5-amino-3-[(2'-hydroxy-1'-tetralyl)methylene]-2-oxindole;
5-amino-3-[(4'-hydroxy-1'-tetralyl)methylene]-2-oxindole;
5-carboxy-3-[(2'-hydroxy-1'-tetralyl)methylene]-2-oxindole;
5-carboxy-3-[(4'-hydroxy-1'-tetralyl)methylene]-2-oxindole;
5-hydroxy-3-[(4',5'-dihydroxy-1'-tetralyl)methylene]-2-oxindole;
5-hydroxy-3-[(4',8'-dihydroxy-1'-tetralyl)methylene]-2-oxindole;
5-amino-3-[(4',5'-dihydroxy-1'-tetralyl)methylene]-2-oxindole;
5-amino-3-[(4',8'-dihydroxy-1'-tetralyl)methylene]-2-oxindole;
5-carboxy-3-[(4',5'-dihydroxy-1'-tetralyl)methylene]-2-oxindole;
3-[(4'-amino-2'-tetralyl)methylene]-2-oxindole;
3-[(4'-carboxy-2'-tetralyl)methylene]-2-oxindole;
5-hydroxy-3-[(2'-tetralyl)methylene]-2-oxindole;
5-amino-3-[(2'-tetralyl)methylene]-2-oxindole;
5-carboxy-3-[(2'-tetralyl)methylene]-2-oxindole;
5-hydroxy-3-[(1'-hydroxy-2'-tetralyl)methylene]-2-oxindole;
5-hydroxy-3-[(3'-hydroxy-2'-tetralyl)methylene]-2-oxindole;
5-hydroxy-3-[(4'-hydroxy-2'-tetralyl)methylene]-2-oxindole;
5-amino-3-[(1'-hydroxy-2'-tetralyl)methylene]-2-oxindole;
5-amino-3-[(3'-hydroxy-2'-tetralyl)methylene]-2-oxindole;
5-amino-3-[(4'-hydroxy-2'-tetralyl)methylene]-2-oxindole;
5-carboxy-3-[(1'-hydroxy-2'-tetralyl)methylene]-2-oxindole;
5-carboxy-3-[(3'-hydroxy-2'-tetralyl)methylene]-2-oxindole;
5-carboxy-3-[(4'-hydroxy-2'-tetralyl)methylene]-2-oxindole;
5-hydroxy-3-[(1',4'-dihydroxy-2'-tetralyl)methylene]-2-oxindole;
5-hydroxy-3-[(4',5'-dihydroxy-2'-tetralyl)methylene]-2-oxindole;
5-hydroxy-3-[(4',8'-dihydroxy-2'-tetralyl)methylene]-2-oxindole;
5-hydroxy-3-[(3',5'-dihydroxy-2'-tetralyl)methylene]-2-oxindole;
5-hydroxy-3-[(3',8'-dihydroxy-2'-tetralyl)methylene]-2-oxindole;
5-amino-3-[(1',4'-dihydroxy-2'-tetralyl)methylene]-2-oxindole;
5-amino-3-[(4',5'-dihydroxy-2'-tetralyl)methylene]-2-oxindole;
5-amino-3-[(4',8'-dihydroxy-2'-tetralyl)methylene]-2-oxindole;
5-amino-3-[(3',5'-dihydroxy-2'-tetralyl)methylene]-2-oxindole;
5-amino-3-[(3',8'-dihydroxy-2'-tetralyl)methylene]-2-oxindole;
5-carboxy-3-[(1',4'-dihydroxy-2'-tetralyl)methylene]-2-oxindole;
5-carboxy-3-[(4',5'-dihydroxy-2'-tetralyl)methylene]-2-oxindole;
5-carboxy-3-[(4',8'-dihydroxy-2'-tetralyl)methylene]-2-oxindole;
5-carboxy-3-[(3',5'-dihydroxy-2'-tetralyl)methylene]-2-oxindole;
5-carboxy-3-[(3',8'-dihydroxy-2'-tetralyl)methylene]-2-oxindole;
5-hydroxy-3-[(1',4',5'-trihydroxy-2'-tetralyl)methylene]-2-oxindole;
5-hydroxy-3-[(1',4',8'-trihydroxy-2'-tetralyl)methylene]-2-oxindole;
3-[(8'-oxo-1',4'-dihydroxy-2'-tetralyl)methylene]-2-oxindole;
5-hydroxy-3-[(5'-quinolyl)methylene]-2-oxindole;
5-amino-3-[(5'-quinolyl)methylene]-2-oxindole;
5-carboxy-3-[(5'-quinolyl)methylene]-2-oxindole;
5-hydroxy-3-[(4'-quinolyl)methylene]-2-oxindole;
5-amino-3-[(4'-quinolyl)methylene]-2-oxindole;
5-carboxy-3-[(4'-quinolyl)methylene]-2-oxindole;
5-hydroxy-3-[(8'-hydroxy-5'-quinolyl)methylene]-2-oxindole;
5-amino-3-[(8'-hydroxy-5'-quinolyl)methylene]-2-oxindole;
5-carboxy-3-[(8'-hydroxy-5'-quinolyl)methylene]-2-oxindole;
5-hydroxy-3-[(8'-hydroxy-4'-quinolyl)methylene]-2-oxindole;
5-amino-3-[(8'-hydroxy-4'-quinolyl)methylene]-2-oxindole; and
5-carboxy-3-[(8'-hydroxy-4'-quinolyl)methylene]-2-oxindole;
5-bromo-3-[(8'-hydroxy-5'-quinolyl)methylene]-2-oxindole;

5-fluoro-3-[(8'-hydroxy-5'-quinolyl)methylene]-2-oxindole;

5-methoxy-3-[(2'-tetralyl)methylene]-2-oxindole;

5-acethoxy-3-[(2'-tetralyl)methylene]-2-oxindole;

5-hydroxy-3-[(4'-hydroxy-1'-tetralyl)methylene]-2-oxindole;

and if the case the pharmaceutically acceptable salts thereof.

A further object of the present invention are the following compounds and the pharmaceutically acceptable salts thereof, which are new and are encompassed by the chemical general formula disclosed by WO 91/13055 and WO 93/01182, but therein not disclosed as specific chemical entities:

3-[(8'-hydroxy-7'-quinolyl)methylene]-2-oxindole;

3-[(5'-hydroxy-4'-quinolyl)methylene]-2-oxindole;

3-[(8'-hydroxy-4'-quinolyl)methylene]-2-oxindole;

3-[(2'-methyl-3'-indolyl)methylene]-2-oxindole;

3-[(5'-cyano-3'-indolyl)methylene]-2-oxindole;

3-[(5'-hydroxy-3'-indolyl)methylene]-2-oxindole;

3-[(5'-methoxy-3'-indolyl)methylene]-2-oxindole;

5-hydroxy-3-[(5'-methoxy-3'-indolyl)methylene]-2-oxindole;

5-amino-3-[(5'-methoxy-3'-indolyl)methylene]-2-oxindole;

5-hydroxy-3-[(2'-methyl-3'-indolyl)methylene]-2-oxindole;

2-cyano-3-(4-quinolyl)acrylamide;

2-cyano-3-(3-indolyl)acrylamide;

2-cyano-3-(1,4-dihydroxy-2-tetralyl)acrylamide;

2-cyano-3-(1,4-dihydroxy-2-tetralyl)thioacrylamide;

2-cyano-3-(2-hydroxy-1-naphthyl)acrylonitrile;

2-cyano-3-(2-naphthyl)acrylamide;

2-cyano-3-(2-naphthyl)thioacrylamide;

2-cyano-3-(3,5-dihydroxy-2-naphthyl)acrylamide; and 2-(4-hydroxyphenyl)-3-(1,4-dimethoxy-2-naphthyl)acrylonitrile;

which when appropriate may be either Z- or E-diastereoisomers or Z, E-mixtures thereof.

The compounds of formula (I), as defined above, and the pharmaceutically acceptable salts thereof can be obtained by a process comprising the condensation of an aldehyde of formula (II)

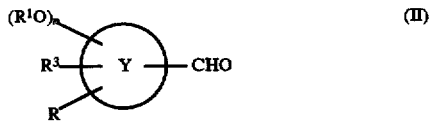

wherein Y, n, R, R¹ and R³ are as defined above, with a compound of formula (III)

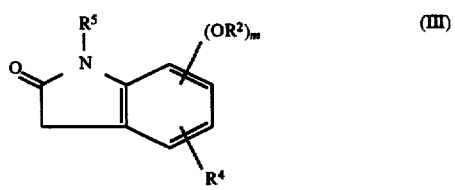

wherein, m, R², R⁴ and R⁵ are as defined above; and if desired, converting a compound of formula (I) into another compound of formula (I), and/or, if desired, converting a compound of formula (I) into a pharmaceutically acceptable salt thereof, and/or, if desired, converting a salt into a free compound, and/or, if desired, separating a mixture of isomers of a compound of formula (I) into the single isomers.

Each of the substituents —OR¹, R³ and —CHO in a compound of formula (II) may be independently on either of the ring moieties of the bicyclic ring systems.

The condensation of a compound of formula (II) with a compound of formula (III) may be carried out according to known methods as herebelow described. For example it may be carried out under the conditions of the Knoevanagel reaction as described, e.g., by G. Jones in Organic Reactions 15, 204(1967). Suitable catalysts are organic bases such as pyridine, piperidine or diethylamine. The condensation may be performed in an inert organic solvent, e.g., pyridine, ethanol, methanol, benzene or dioxane at temperatures ranging from about 0° C. to about 100° C. Preferably the reaction is carried out in hot ethanol solution in the presence of piperidine catalyst.

A compound of formula (I) can be converted into another compound of formula (I) according to known methods. For example the de-etherification of a compound of formula (I) wherein one or more —OR¹ and/or —OR² methoxy groups are present to obtain the corresponding hydroxy substituted derivative can be carried out for example with boron tribromide as described by J. F. N. McOmie in Tetrahedron 24, 2289 (1968). The reaction may be performed in an inert organic solvent such as dichloromethane or benzene under an inert atmosphere (e.g. nitrogen) at temperatures ranging from about −78° C. to about room temperature.

The conversion of a compound of formula (I) in which R³ and/or R⁴ is nitro into the corresponding compound of formula (I), wherein R³ and/or R⁴ is amino, may be carried out following known methods, for example with a variety of reducing agents, e.g. sodium sulfide in hydroalcoholic solution, metallic iron with ammonium chloride in aqueous solvent, or for instance, catalytic hydrogenation using e.g. palladium charcoal catalyst at low hydrogen pressure in an inert organic solvent.

The alkylation of a compound of formula (I), wherein —OR¹ and/or —OR² is hydroxy, so as to obtain the corresponding compound of formula (I), wherein —OR¹ and/or —OR² is $C_1$–$C_6$ alkoxy, may be obtained, e.g., by reaction with sodium hydride and $C_1$–$C_6$ alkyl iodide in a high boiling aromatic solvent such as xylene.

The acylation of a compound of formula (I), wherein —OR¹ and/or —OR² is hydroxy, in order to obtain the corresponding compound of formula (I), wherein —OR¹ and/or —OR² is a $C_1$–$C_6$ alkanoyloxy, can be performed, e.g., by reaction with a suitable carboxylic acid anhydride in the presence of a basic agent at temperatures ranging from room temperature to reflux temperatures.

The optional salification of a compound of formula (I) as well as the conversion of a salt into a free compound, and the separation of a mixture of isomers into the single isomers may be carried out by conventional methods. For example the separation of a mixture of geometric isomers, e.g. Z- and E-isomers, may be carried out by fractional crystallization from a suitable solvent or by chromatography, either column chromatography or HPLC.

The compounds of formula (II) may be obtained according to known methods from compounds of formula (IV)

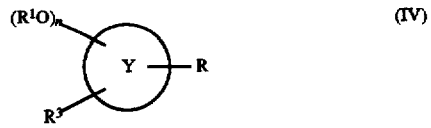

wherein Y, R, n, R³ and R¹ are as defined above.

For example when compound (IV) contains phenolic groups, i.e. R¹O— is hydroxy, the well known Reimer-Tiemann method can be applied. Thus the phenolic compound is treated with chloroform and alkali hydroxides in an aqueous or hydroalcoholic solution. Another useful method for the synthesis of aromatic or phenolic aldehydes has been described by H. Gross et al. in Chem. Ber. 96, 308 (1963). Accordingly a compound of formula (IV), in which the OR¹ group may be present or not, can be treated with a dichloromethyl ether, e.g. dichloromethyl methyl ether, in the presence of a Friedel-Crafts catalyst such as titanium tetrachloride or aluminium trichloride in an inert solvent like dichloromethane or nitrobenzene at temperatures ranging from about 0° C. to about 60° C.

The compounds of formula (III) and (IV) are known or may be obtained by known methods.

The new oxindolylidene derivatives and the pharmaceutically acceptable salts thereof, for the first time herein disclosed and encompassed by WO 91/13055 (U.S. Pat. No. 5,374,652) and WO 93/01182, (U.S. Pat. No. 5,409,944) can be obtained by following the same procedure described above for the preparation of a compound of formula (I). Of course a suitable quinoline- or indole-carboxaldehyde has to be chosen as will be easily appreciated by the skilled people in the art.

Similarly the novel acrylamide, thioacrylamide and acrylonitrile derivatives encompassed by the general formula (I) disclosed in WO 91/13055, and mentioned herein for the first time as specific chemical entities, can be obtained by following the procedures described in WO 91/13055 by reacting a suitable quinoline-, tetralin- or naphthalene-carboxaldehyde with cyanoacetamide, cyanothioacetamide or 4-hydroxybenzylcyanide, respectively. When in the new compounds of the present invention and in the intermediate products used for their preparation there are groups present which need to be protected before the above-described reactions are performed, they may be protected before the reaction takes place and then deprotected at the end of the reaction, according to well known methods in organic chemistry. The new compounds provided by the present invention, namely both the compounds of formula (I) as defined above and the new compounds herein specifically disclosed and encompassed by WO 91/13055 and WO 93/01182, are referred to as "the compounds of the invention".

Pharmacology

The compounds of the invention possess specific tyrosine kinase inhibiting activity. It is believed that tyrosine kinase inhibitors may be of great importance in the control of uncontrolled cellular reproduction, i.e. in cellular reproduction disorders. Hence the compounds according to the present invention can be useful in the treatment of pathological proliferation disorders in mammals, including humans.

A human or animal, e.g. a mammal, can thus be treated by a method comprising the administration thereto of a therapeutically effective amount of one of the compounds of the invention. In this way the condition of the human or animal may be improved. Amelioration of the disease state or disorder from which the human or animal is suffering can be achieved. Typical examples of such disorders are tumours, including leukaemia such as myeloblastic leukaemia, lymphoma, sarcoma, neuroblastoma, Wilm's tumour and malignant neoplasm of the bladder, breast, lung or thyroid; and psoriasis. The compounds of the invention can also be useful in inhibiting the development of the atheromatous plaque and in the control of angiogenesis and as antimetastatic agents.

Recent studies on the molecular basis or neoplastic transformation have identified a family of genes, designated oncogenes, whose aberrant expression causes tumorigenesis. For example, the RNA tumor viruses possess such an oncogene sequence whose expression determines neoplastic conversion of infected cells. Several of their oncogene-encoded proteins, such as $pp60^{v-arc}$, $p70^{gag-yes}$, $p130^{gag-fps}$ and $P70^{gag-fgr}$ display protein tyrosine kinase activity, that is they catalyse the transfer of the γ-phosphate from adenosine triphosphate (ATP) to tyrosine residues in protein substrate. In normal cells, several growth factor receptors, for example the receptors for PDGF, EGF, α-TGF and insulin, display tyrosine kinase activity.

Binding of the growth factor (GF) activates the receptor tyrosine kinase to undergo autophosphorylation and to phosphorylate closely adjacent molecules on tyrosine. Therefore, it is thought that the phosphorylation of these tyrosine kinase receptors plays an important role in signal transduction and that the principal function of tyrosine kinase activity in normal cells is to regulate cell growth. Perturbation of this activity by oncogenic tyrosine kinases that are either over-produced and/or display altered substrate specificity may cause loss of growth control and/or neoplastic transformation. Accordingly, a specific inhibitor of tyrosine kinase can be useful in investigating the mechanism of carcinogenesis, cell proliferation and differentiations and it can be effective in prevention and chemotherapy of cancer and in other pathological proliferative conditions, for instance as mentioned above. The tyrosine specific protein kinase activity of these compounds is shown e.g. by the fact that they are active in the following in vitro and in vivo tests described herebelow.

In Vitro ASSAY p45 v-abl kinase purification. The enzyme used in our test was the p45 v-abl tyrosine kinase which represents the catalytic domain of the Abelson tyrosine kinase (isolated from the Abelson murine leukemia virus). The p45 v-abl kinase was produced and isolated as described by Wang et al. in J. Biol. Chem. 260, 64 (1985) and by Ferguson et al. in J. Biol. Chem. 260, 3652 (1985) and in Biochem. J. 257, 321 (1989).

p45 v-abl Kinase Assay. (Val⁵)-Angiotensin II phosphorylation was performed by incubation with 40 ng of purified abl-kinase and $(\gamma-^{32}P)$-ATP, in 50 µl of buffer containing Tris-HCl 25 mM, pH 8.0, $MgCl_2$ 10 mM and dithiothreitol 0.1 mM (kinase buffer). The reaction mixture was incubated for the indicated time at 30° C. and the reaction stopped by adding 50 µl of 5% trichloroacetic acid. After a brief incubation on ice, tubes were centrifuged. The supernatants were spotted on phosphocellulose paper squares (Whatman P-81) and washed extensively in acetic acid. The radioactivity bound to dried phosphocellulose squares was measured in a liquid scintillation counter. $IC_{50}$ values were calculated from triplicate determinations of each experimental point. Each inhibitor was tested at concentrations ranging from 0 to 400 µg in the presence of fixed concentrations of peptide (2 mM) and ATP (50 µM).

In Vivo ASSAY

K562 cell growth inhibition assay. 1 ml of K562 cells, grown in suspension, were incubated for 66 h with or without 10% foetal calf serum in the presence of 1 µCi of [³-H]-Thymidine. Cells were harvested, washed three times in cold PBS and treated with 5% trichloroacetic acid for 5 min on ice. After a wash in ethanol: ether 2:1, the DNA was extracted by 0.5N NaOH for 2 h at room temperature. The extract was counted in a liquid scintillation counter.

The inhibitory activity data for a representative group of compounds according to the present invention, obtained both in the in vitro p45 v-abl kinase assay and in the in vivo human chronic myeloid leukemia K 562 cell growth inhibition assay described above, are set out in following Table 1.

TABLE 1

Inhibition of p45 v-abl kinase and K562 cell growth.

| Compound | $IC_{50}$ (µM) | |
| --- | --- | --- |
| | v-abl | K562 |
| FCE 27518 | 6.9 | 1.2 |
| FCE 27566 | 15.6 | 2.2 |
| FCE 27565 | 2.4 | — |
| FCE 27866 | 5.2 | 8.75 |
| FCE 27564 | 0.8 | 4.15 |
| FCE 27996 | 2.6 | 0.62 |
| FCE 28359 | 0.39 | 8.15 |
| FCE 28436 | 0.305 | 14.50 |
| FCE 28337 | 2.32 | 11.5 |
| FCE 28360 | 4.7 | 6.25 |

In the Table:
FCE 27518 means: 5-amino-3-[(8'-hydroxy-5'-quinolyl)methylene]-2-oxindole;
FCE 27566 means: 3-[(2'-methyl-3'-indolyl)methylene]-2-oxindole;
FCE 27565 means: 3-[(5'-cyano-3'-indolyl)methylene]-2-oxindole;
FCE 27866 means: 3-[(5'-hydroxy-3'-indolyl)methylene]-2-oxindole;
FCE 27564 means: 3-[(5'-methoxy-3'-indolyl)methylene]-2-oxindole;
FCE 27996 means: 5-bromo-3-[(8'-hydroxy-5'quinolyl)methylene]-2-oxindole;
FCE 28359 means: 5-hydroxy-3-[(5'-methoxy-3'-indolyl)methylene]-2-oxindole;
FCE 28436 means: 5-amino-3-[(5'-methoxy-3'-indolyl)methylene]-2-oxindole;
FCE 28337 means: 5-hydroxy-3-[(4'-hydroxy-1'-tetralyl)methylene]-2-oxindole;
FCE 28360 means: 5-amino-3-[(1',4'-dihydroxy-2'-tetralyl)methylene]-2-oxindole.

As can be appreciated from the activity data shown in Table 1, the compounds according to the invention are endowed with valuable biological properties.

In view of their high activity and low toxicity, the compounds of the invention can be used safely in medicine.

The compounds of the invention can be administered in a variety of dosage forms, e.g. orally, in the form of tablets, capsules, sugar or film-coated tablets, liquid solutions or suspensions; rectally, in the form of suppositories; parenterally, e.g. intramuscularly, or by intravenous injection or infusion; or topically.

The dosage depends on the age, weight, condition of the patient and administration route; for example, the dosage adopted for oral administration of the compounds 3-[(5'-methoxy-3'-indolyl)methylene]-2-oxindole and 5-bromo-3-[(8'-hydroxy-5'-quinolyl)methylene]-2-oxindole to adult humans may range from about 10 to about 150–200 mg per dose, from 1 to 5 times daily. Of course, these dosage regimens may be adjusted to provide the optimal therapeutic response.

The invention includes pharmaceutical compositions comprising a compound of the invention or a pharmaceutically acceptable salt thereof in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating or film-coating processes.

The liquid dispersion for oral administration may be e.g. syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusion may contain as carrier, for example, sterile water or, preferably, they may be in the form of sterile, aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin.

Compositions for topical application, e.g. creams, lotions, or pastes, can be prepared by mixing the active ingredient with a conventional oleaginous or emulsifying excipient.

Object of the present invention is also the use of a compound of formula (I)

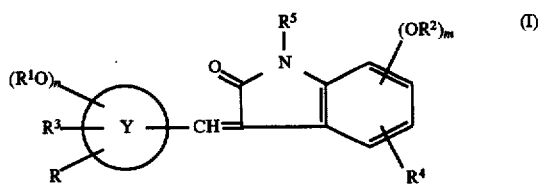

wherein
Y is a bicyclic ring system chosen from naphthalene, tetralin, quinoline and isoquinoline;
R is hydrogen or an oxo (=O) group when Y is tetralin, or R is hydrogen when Y is naphthalene, quinoline or isoquinoline;
each of $R^1$ and $R^2$ independently is hydrogen, $C_1$–$C_6$ alkyl or $C_2$–$C_6$ alkanoyl;
m is zero, 1 or 2;
n is zero, 1, 2 or 3;
each of $R^3$ and $R^4$ independently is hydrogen, halogen, cyano, $C_1$–$C_6$ alkyl, carboxy, nitro or —$NR^6R^7$ in which each of $R^6$ and $R^7$ independently is hydrogen or $C_1$–$C_6$ alkyl;

$R^5$ is hydrogen or $C_1-C_6$ alkyl; and the pharmaceutically acceptable salts thereof; and wherein a) when at the same time Y is naphthalene; $R^3$ is hydrogen, halogen, cyano or $C_1-C_6$ alkyl; $R^5$ is hydrogen; m is zero and n, R and $R^1$ are as defined above, then $R^4$ is other than hydrogen;

b) when at the same time Y is quinoline or isoquinoline; $R_3$ is hydrogen, halogen, cyano or $C_1-C_6$ alkyl; n is zero, 1 or 2; $R^5$ is hydrogen; m is zero and R and $R^1$ are as defined above, then $R^4$ is other than hydrogen; and c) when at the same time Y is tetralin in which only the benzene moiety is substituted, $R^3$ is hydrogen, halogen, cyano or $C_1-C_6$ alkyl; n is zero, 1 or 2; $R^5$ is hydrogen; m is zero, R is hydrogen and $R^1$ is as defined above, then $R^4$ is other than hydrogen;

in the preparation of a pharmaceutical composition for use as tyrosine kinase inhibitor, in particular in the treatment of the pathological disorders cited above.

A further object of the present invention is a combined method of treatment of cancer or of amelioration of the conditions of mammals, including humans, suffering from cancer, said method comprising administering 1) a compound of the invention, or a pharmaceutically acceptable salt thereof, and 2) an additional antitumor agent, in amounts and close enough together in time sufficient to produce a therapeutically useful effect.

The present invention also provides products containing a compound of the invention, or a pharmaceutically acceptable salt thereof, and an additional antitumour agent as a combined preparation for simultaneous, separate or sequential use in anti-cancer therapy.

The term "antitumor agent" is meant to comprise both a single antitumor drug and "cocktails" i.e. a mixture of such drugs, according to the clinical practice.

Examples of antitumor agents that can be formulated with a compound of the invention or alternatively, can be administered in a combined method of treatment, include doxorubicin, daunomycin, epirubicin, idarubicin, etoposide, fluoro-uracil, melphalan, cyclophosphamide, bleomycin, vinblastin and mitomycin or a mixtures of two or more thereof.

The compounds of the invention can therefore be used in a treatment to ameliorate a cancer. They may be administered to a patient suffering from a cancer treatable with an antitumor agent, for example an anthracycline glycoside such as doxorubicin, daunomycin, epirubicin or idarubicin as mentioned above, together with the antitumor agent.

A compound of the invention and an antitumor agent such as an anthracycline glycoside can be administered to improve the condition of a patient having a leukaemia such as myeloblastic leukaemia, lymphoma, sarcoma, neuroblastoma, Wilm's tumor or malignant neoplasm of the bladder, breast, lung or thyroid.

The following examples illustrate but do not limit the invention.

EXAMPLE 1

5-hydroxy-3-[(8'-hydroxy-5'-quinolyl)methylene]-2-oxindole

A solution of 8-hydroxyquinoline-5-carboxaldehyde (173 mg, 1 mmol), 5-hydroxy-2-oxindole (149 mg, 1 mmol) and piperidine (60 mg, 0.7 mmol) in absolute ethanol (10 ml) was heated for 3 h at 60°–70° C. under nitrogen. Then the reaction mixture was chilled and evaporated under vacuum to dryness. The residue was submitted to column chromatography over silica gel using dichloromethane/ethanol 4% as eluant to give pure title compound in about 60% yield.

Alternatively, the reaction mixture was concentrated under vacuum and then chilled to 0°–5° C., the precipitate filtered, the residue washed with ice-cooled ethanol and finally dried under vacuum. Compounds of higher purity are obtained by further crystallization from ethanol.

| $C_{18}H_{12}N_2O_3$ | requires: | C 71.05 | H 3.98 | N 9.20 |
|---|---|---|---|---|
| | found: | C 71.01 | H 3.85 | N 9.15 |

MS m/z 304

NMR δ ppm: 6.5–6.7 (m,3H), 7.20 (d,1H), 7.62 (dd,1H), 7.83 (d,1H), 7.93 (s,1H), 8.33 (dd,1H), 8.85 (bs,1H), 8.93 (dd,1H), 10.30 (bs,1H).

According to the above described procedure, the following compounds can be prepared:

5-amino-3-[(8'-hydroxy-5'-quinolyl)methylene]-2-oxindole;

| $C_{18}H_{12}N_2O_2$ | requires: | C 74.98 | H 4.20 | N 9.72 |
|---|---|---|---|---|
| | found: | C 74.76 | H 4.31 | N 9.43 |

MS m/z 288

NMR δ ppm: 6.4–6.6 (mm,3H), 7.18 (d,1H), 7.62 (dd,1H), 7.84 (d,1H), 7.87 (s,1H), 8.34 (dd,1H), 8.93 (dd,1H), 10.14 (bs,1H).

3-[(2'-methyl-3'-indolyl)methylene]-2-oxindole

| $C_{18}H_{14}N_2O$ | requires: | C 78.81 | H 5.14 | N 10.21 |
|---|---|---|---|---|
| | found: | C 78.56 | H 5.01 | N 10.11 |

MS m/z 274

NMR δ ppm: 2.46 (s,3H), 6.7–6.8 (m,2H), 6.85 (d,1H), 7.0–7.2 (m,4H), 7.41 (d,1H), 7.80 (s,1H), 10.48 (bs,1H), 11.86 (bs,1H).

3-[(5'-cyano-3'-indolyl)methylene]-2-oxindole

| $C_{18}H_{11}N_3O$ | requires: | C 75.77 | H 3.89 | N 14.73 |
|---|---|---|---|---|
| | found: | C 75.71 | H 3.55 | N 14.51 |

MS m/z 285

NMR δ ppm: 6.8–7.2 (m,3H), 7.57 (dd,1H), 7.69 (d,1H), 7.95 (d,1H), 8.21 (s,1H), 8.85 (d,1H), 9.52 (s,1H), 10.62 (bs,1H), 12.4 (bs,1H).

3-[(5'-hydroxy-3'-indolyl)methylene]-2-oxindole

| $C_{17}H_{12}N_2O_2$ | requires: | C 73.89 | H 4.38 | N 10.14 |
|---|---|---|---|---|
| | found: | C 73.55 | H 4.36 | N 9.97 |

MS m/z 276

NMR δ ppm: 6.75 (m,1H), 6.82 (d,1H), 6.9–7.0 (m,1H), 7.0–7.2 (m,1H), 7.29 (d,1H), 7.42 (d,1H), 7.80 (d,1H), 7.97 (s,1H), 8.96 (s,1H), 9.34 (d,1H), 10.42 (s,1H), 11.8 (bs,1H).

3-[(5'-methoxy-3'-indolyl)methylene]-2-oxindole

| $C_{18}H_{14}N_2O_2$ | requires: | C 74.47 | H 4.86 | N 9.65 |
|---|---|---|---|---|
| | found: | C 74.35 | H 4.72 | N 9.54 |

MS m/z 290

NMR δ ppm: 3.87 (s,3H), 6.8–6.9 (m,2H), 7.12 (ddd,1H), 7.38 (d,1H), 7.72 (d,1H), 7.91 (d,1H), 8.13 (s,1H), 9.40 (s,1H), 10.49 (bs,1H), 11.88 (bs,1H).

3-[(8'-hydroxy-7'-quinolyl)methylene]-2-oxindole

| $C_{18}H_{12}N_2O_2$ | requires: | C 74.98 | H 4.20 | N 9.72 |
|---|---|---|---|---|
| | found: | C 79.81 | H 4.31 | N 9.43 |

MS m/z 288

NMR δ ppm: 6.8–6.9 (m,2H), 7.21 (t,1H), 7.48 (m,2H), 7.64 (dd,1H), 7.81 (d,1H), 7.89 (s,1H), 8.38 (dd,1H), 8.91 (dd,1H), 10.6 (bs,1H).

5-hydroxy-3-[(2'-methyl-3'-indolyl)methylene]-2-oxindole

NMR δ ppm: 2.42 (s,3H), 6.30 (d,1H), 6.54 (dd,1H), 6.63 (d,1H), 7.0–7.2 (m,3H), 7.41 (d,1H), 7.73 (s,1H), 8.71 (s,1H), 10.16 (s,1H), 11.79 (s,1H).

3-[(4'-amino-1'-tetralyl)methylene]-2-oxindole;
3-[(4'-dimethylamino-1'-tetralyl)methylene]-2-oxindole;
3-[(4'-carboxy-1'-tetralyl)methylene]-2-oxindole;
5-hydroxy-3-[(1'-tetralyl)methylene]-2-oxindole;
5-amino-3-[(1'-tetralyl)methylene]-2-oxindole;
5-carboxy-3-[(1'-tetralyl)methylene]-2-oxindole;
5-hydroxy-3-[(2'-hydroxy-1'-tetralyl)methylene]-2-oxindole;
5-hydroxy-3-[(4'-hydroxy-1'-tetralyl)methylene]-2-oxindole NMR δ ppm: 1.69 (m,4H), 2.5–2.7 (m,4H), 6.57 (dd,1H), 6.62 (d,1H), 6.72 (d,1H), 6.88 (d,1H), 7.26 (d,1H), 7.53 (s,1H), 8.87 (s,1H), 9.8 (bs,1H), 10.17 (s,1H).

5-amino-3-[(2'-hydroxy-1'-tetralyl)methylene]-2-oxindole;
5-amino-3-[(4'-hydroxy-1'-tetralyl)methylene]-2-oxindole;
5-carboxy-3-[(2'-hydroxy-1'-tetralyl)methylene]-2-oxindole;
5-carboxy-3-[(4'-hydroxy-1'-tetralyl)methylene]-2-oxindole;
5-hydroxy-3-[(4',5'-dihydroxy-1'-tetralyl)methylene]-2-oxindole;
5-hydroxy-3-[(4',8'-dihydroxy-1'-tetralyl)methylene]-2-oxindole;
5-amino-3-[(4',5'-dihydroxy-1'-tetralyl)methylene]-2-oxindole;
5-amino-3-[(4',8'-dihydroxy-1'-tetralyl)methylene]-2-oxindole;
5-carboxy-3-[(4',5'-dihydroxy-1'-tetralyl)methylene]-2-oxindole;
3-[(4'-amino-2'-tetralyl)methylene]-2-oxindole;
3-[(4'-carboxy-2'-tetralyl)methylene]-2-oxindole;
5-hydroxy-3-[(2'-tetralyl)methylene]-2-oxindole;
5-amino-3-[(2'-tetralyl)methylene]-2-oxindole;
5-carboxy-3-[(2'-tetralyl)methylene]-2-oxindole;
5-hydroxy-3-[(1'-hydroxy-2'-tetralyl)methylene]-2-oxindole;
5-hydroxy-3-[(3'-hydroxy-2'-tetralyl)methylene]-2-oxindole;
5-hydroxy-3-[(4'-hydroxy-2'-tetralyl)methylene]-2-oxindole;
5-amino-3-[(1'-hydroxy-2'-tetralyl)methylene]-2-oxindole;
5-amino-3-[(3'-hydroxy-2'-tetralyl)methylene]-2-oxindole;
5-amino-3-[(4'-hydroxy-2'-tetralyl)methylene]-2-oxindole;
5-carboxy-3-[(1'-hydroxy-2'-tetralyl)methylene]-2-oxindole;
5-carboxy-3-[(3'-hydroxy-2'-tetralyl)methylene]-2-oxindole;
5-carboxy-3-[(4'-hydroxy-2'-tetralyl)methylene]-2-oxindole;
5-hydroxy-3-[(1',4'-dihydroxy-2'-tetralyl)methylene]-2-oxindole;
5-hydroxy-3-[(4',5'-dihydroxy-2'-tetralyl)methylene]-2-oxindole;
5-hydroxy-3-[(4',8'-dihydroxy-2'-tetralyl)methylene]-2-oxindole;
5-hydroxy-3-[(3',5'-dihydroxy-2'-tetralyl)methylene]-2-oxindole;
5-hydroxy-3-[(3',8'-dihydroxy-2'-tetralyl)methylene]-2-oxindole;
5-amino-3-[(1',4'-dihydroxy-2'-tetralyl)methylene]-2-oxindole NMR δ ppm: 1.69 (m,4H), 2.58 (m,4H), 6.86 (s,1H), 6.94 (d,1H), 7.15 (dd,1H), 7.60 (d,1H), 7.75 (s,1H), 8.4 (bs,1H), 8.9 (bs,1H), 9.7 (bs,3H), 10.71 (s,1H).

5-amino-3-[(4',5'-dihydroxy-2'-tetralyl)methylene]-2-oxindole;
5-amino-3-[(4',8'-dihydroxy-2'-tetralyl)methylene]-2-oxindole;
5-amino-3-[(3',5'-dihydroxy-2'-tetralyl)methylene]-2-oxindole;
5-amino-3-[(3',8'-dihydroxy-2'-tetralyl)methylene]-2-oxindole;
5-carboxy-3-[(1',4'-dihydroxy-2'-tetralyl)methylene]-2-oxindole;
5-carboxy-3-[(4',5'-dihydroxy-2'-tetralyl)methylene]-2-oxindole;
5-carboxy-3-[(4',8'-dihydroxy-2'-tetralyl)methylene]-2-oxindole;
5-carboxy-3-[(3',5'-dihydroxy-2'-tetralyl)methylene]-2-oxindole;
5-carboxy-3-[(3',8'-dihydroxy-2'-tetralyl)methylene]-2-oxindole;
5-hydroxy-3-[(1',4',5'-trihydroxy-2'-tetralyl)methylene]-2-oxindole;
5-hydroxy-3-[(1',4',8'-trihydroxy-2'-tetralyl)methylene]-2-oxindole;
3-[(8'-oxo-1',4'-dihydroxy-2'-tetralyl)methylene]-2-oxindole NMR δ ppm: 2.03 (m,2H), 2.70 and 2.89 (two m,4H), 6.7–7.0 (m,2H), 7.1–7.3 (m,1H), 7.51 (s,1H), 7.54 (d,1H), 7.58 (d,1H), 7.61 (s,1H), 7.87 (s,1H), 8.46 (s,1H), 9.38 (s,1H), 9.56 (s,1H), 10.58 (s,1H), 10.59 (s,1H), 12.5 (bs,1H), 12.8 (bs,1H).

5-hydroxy-3-[(5'-quinolyl)methylene]-2-oxindole;
5-amino-3-[(5'-quinolyl)methylene]-2-oxindole;
5-carboxy-3-[(5'-quinolyl)methylene]-2-oxindole;
5-hydroxy-3-[(4'-quinolyl)methylene]-2-oxindole;

5-amino-3-[(4'-quinolyl)methylene]-2-oxindole;

5-carboxy-3-[(4'-quinolyl)methylene]-2-oxindole;

5-carboxy-3-[(8'-hydroxy-5'-quinolyl)methylene]-2-oxindole;

5-hydroxy-3-[(8'-hydroxy-4'-quinolyl)methylene]-2-oxindole;

5-amino-3-[(8'-hydroxy-4'-quinolyl)methylene]-2-oxindole;

5-carboxy-3-[(8'-hydroxy-4'-quinolyl)methylene]-2-oxindole;

5-bromo-3-[(8'-hydroxy-5'-quinolyl)methylene]-2-oxindole

NMR δ ppm: 6.76 (d,1H), 6.83 (d,1H), 7.12 (d,1H), 7.17 (d,1H), 7.22 (d,1H), 7.3–7.4 (m,2H), 7.6–7.7 (m,2H), 7.89 (d,1H), 8.08 (s,1H), 8.17 (d,1H), 8.36 (dd,1H), 8.46 (s,1H), 8.8–9.0 (m,4H), 10.66 (s,1H), 10.77 (s,1H).

5-fluoro-3-[(8'-hydroxy-5'-quinolyl)methylene]-2-oxindole

NMR δ ppm: 6.8–6.9 (m,2H), 7.04 (ddd,1H), 7.22 (d,1H), 7.63 (dd,1H), 7.89 (d,1H), 8.08 (s,1H), 8.37 (dd,1H), 8.94 (dd,1H), 10.5 (bs,1H), 10.65 (s,1H).

3-[(5'-hydroxy-4'-quinolyl)methylene]-2-oxindole;

3-[(8'-hydroxy-4'-quinolyl)methylene]-2-oxindole;

5hydroxy-3-[(5'-methoxy-3'-indolyl)methylene]-2-oxindole

NMR δ ppm: 3.86 (s,3H), 6.5–6.7 (m,2H), 6.82 (dd,1H), 7.36 (m,2H), 7.68 (d,1H), 7.99 (s,1H), 8.82 (s,1H), 9.37 (d,1H), 10.15 (s,1H), 11.8 (bs,1H).

5-amino-3-[(5'-methoxy-3'-indolyl)methylene]-2-oxindole

NMR δ ppm: 3.87 (s,3H), 6.87 (dd,1H), 6.90 (d,1H), 7.07 (dd,1H), 7.42 (d,1H), 7.66 (d,1H), 7.81 (d,1H), 8.18 (s,1H), 9.44 (d,1H), 9.65 (bs,3H), 10.67 (s,1H), 12.03 (d,1H), and 5-hydroxy-3-[(2'-methyl-3'-indolyl)methylene]-2-oxindole

EXAMPLE 2

5-hydroxy-3-[(1'-tetralyl)methylene]-2-oxindole

To a stirred solution of 5-methoxy-3-[(1'-tetralyl)methylene]-2-oxindole (305 mg, 1 mmol) in anhydrous dichloromethane (10 ml) was added at −78° C. under nitrogen, over a period of 10 min, a 1.0M solution of boron tribromide in dichloromethane (3 ml, 3 mmol). The resulting mixture was stirred for another 1 h at −78° C. and then allowed to warm up to room temperature. After stirring for 1.5 h at 20°–25° C. the mixture was cooled to −10° C. and then quenched by dropwise addition of water (10 ml) over a 10-min period. After addition of ethyl acetate the organic layer was separated, washed with water, dried with Na₂SO₄ and evaporated under vacuum to dryness. The residue was crystallized from ethanol thus giving pure title compound in 70% yield.

| $C_{19}H_{17}NO_2$ | requires: | C 78.30 | H 5.88 | N 4.81 |
|---|---|---|---|---|
|  | found: | C 78.15 | H 5.75 | N 4.71 |

MS m/z 291

IR cm⁻¹: 3600–2600 (NH,OH), 1655 (amide), 1610 (amide), 1585, 1535 (C=C).

EXAMPLE 3

5-amino-3-[(1'-tetralyl)methylene]-2-oxindole

To a solution of 5-nitro-3-[(1'-tetralyl)methylene]-2-oxindole (320 mg, 1 mmol) in anhydrous ethanol (20 ml) was added palladium on charcoal (20 mg) and the mixture was hydrogenated at room temperature and atmospheric pressure until 3 equivalent of hydrogen has been taken up. The hydrogen uptake was graphed as a function of time. The catalyst was filtered and the solution concentrated under vacuum until crystallization began. Then the mixture was cooled to 0°–5° C., filtered, the residue washed with ice-cooled ethanol and dried under vacuum. Thus almost pure title compound was obtained in about 80% yield.

| $C_{19}H_{18}N_2O$ | requires: | C 78.59 | H 6.25 | N 9.65 |
|---|---|---|---|---|
|  | found: | C 78.45 | H 6.13 | N 9.55 |

MS m/z 290

IR cm⁻¹: 3400–3200 (NH), 1660 (amide), 1610 (amide) 1580, 1530 (C=C).

EXAMPLE 4

5-methoxy-3-[(2'-tetralyl)methylene]-2-oxindole

To a suspension of 95% sodium hydride (28 mg, 1.1 mmol) in DMF (10 ml) cooled with an ice-propanol bath was added over 15 min with stirring a solution of 5-hydroxy-3-[(2'-tetralyl)methylene]-2-oxindole (291 mg, 1 mmol) in DMF (5 ml). When the evolution of hydrogen stopped, a solution of iodomethane (156 mg, 1.1 mmol) in DMF (5 ml) was added over 15 min and the mixture was stirred at room temperature for 3 h. Most of the DMF was distilled off in vacuum, water was then added to the residue and the product extracted into ethylacetate. The organic solution containing the desired product was dried, the solvent evaporated and the remaining oil was crystallized by trituration with ethanol. Thus pure title compound was obtained in about 60% yield.

| $C_{20}H_{19}NO_2$ | requires: | C 78.66 | H 6.27 | N 4.59 |
|---|---|---|---|---|
|  | found: | C 78.51 | H 6.11 | N 4.35 |

MS m/z 305

IR cm⁻¹: 3400–3200, 1655, 1605 (amide), 1580, 1530 (C=C).

EXAMPLE 5

5-acetoxy-3-[(2'-tetralyl)methylene]-2-oxindole

To a cooled solution of 5-hydroxy-3-[(2'-tetralyl)methylene]-2-oxindole (291 mg, 1 mmol) in dry pyridine (0.5 ml) was added acetic anhydride (306 mg, 3 mmol) and the mixture maintained at 0°–5° C. overnight. Thereupon the mixture was concentrated under vacuum, the residue dissolved in dichloromethane, the organic layer washed with water and then evaporated under reduced pressure. The crude product was crystallized from chloroform/methanol to yield almost pure title compound in about 80% yield.

| $C_{21}H_{19}NO_3$ | requires: | C 75.66 | H 5.74 | N 4.20 |
|---|---|---|---|---|
|  | found: | C 75.59 | H 5.81 | N 4.15 |

MS m/z 333.

EXAMPLE 6

1,4-dihydroxy-2-tetralincarboxaldehyde

To a solution of 1,4-dihydroxy-tetralin (1.640 g, 0.010 mol) in dichloromethane (50 ml) was added titanium tetrachloride (5.69 g, 0.03 mol). Then 1,1-dichlorodimethyl ether (1.73 g, 0.015 mol) was added dropwise under vigorous stirring and the reaction mixture stirred for another 3 h at room temperature. Finally 5% hydrochloric acid (10 ml) was added under ice-cooling. The organic phase was separated and the residual aqueous phase repeatedly extracted with ether. The combined organic phases are washed with saturated saline solution, dried over sodium sulfate and evaporated under vacuum. The residue was crystallized from benzene or alternatively submitted to flash chromatography on silica gel with benzene/ethylacetate 85:15 to afford pure title compound in about 60% yield (1.080 g), m.p. 145° C.

MS m/z 180

NMR δ ppm: 10.4 (bs, OH), 9.7 (s, CHO), 9.1 (bs, OH), 6.9 (s, H arom), 2.8 (m, 5-$CH_2$, 8-$CH_2$), 1.9 (m, 6-$CH_2$, 7-$CH_2$).

EXAMPLE 7

By proceeding according to the technique of above Example 1 and Examples 1, 2 and 7 of WO 91/13055 and starting from a suitable quinoline-, tetralin- or naphthalene-carboxaldehyde and cyanoacetamide, cyanothioacetamide or 4-hydroxybenzylcyanide the following compounds can be obtained.

2-(4-hydroxyphenyl)-3-(1,4-dimethoxy-2-naphthyl) acrylonitrile

| $C_{16}H_{14}N_2O_3$ | requires: | C 68.07 | H 5.00 | N 9.93 |
|---|---|---|---|---|
| | found: | C 67.98 | H 5.02 | N 9.92 |

MS m/z 282
NMR δ ppm: 3.90 (3H,s), 3.99 (3H,s), 7.60 (1H,s), 7.70 (2H,m), 7.8, 8.0 (2H, two S), 8.15 (2H,m), 8.49 (1H,s).

2-cyano-3-(4-quinolyl)acrylamide

| $C_{13}H_9N_3O$ | requires: | C 69.95 | H 4.06 | N 18.82 |
|---|---|---|---|---|
| | found: | C 69.86 | H 4.01 | N 18.75 |

MS m/z 223
IR $cm^{-1}$: 3400, 3299 (NH), 2210 (CN), 1680 (CO), 1610, 1590, 1580 (C=C).

2-cyano-3-(3-indolyl)acrylamide

| $C_{12}H_9N_3O$ | requires: | C 68.24 | H 4.29 | N 19.89 |
|---|---|---|---|---|
| | found: | C 68.11 | H 4.21 | N 19.85 |

MS m/z 211
IR $cm^{-1}$: 3400, 3150 (NH), 2220 (CN), 1680 (CO), 1605, 1590, 1580 (C=C).

2-cyano-3-(1,4-dihydroxy-2-tetralyl)acrylamide

| $C_{14}H_{14}N_2O_3$ | requires: | C 65.10 | H 5.46 | N 10.85 |
|---|---|---|---|---|
| | found: | C 65.16 | H 5.58 | N 10.67 |

MS m/z 258
IR $cm^{-1}$: 3200–3400 (NH,OH), 2210 (CN), 1680 (CO), 1610, 1595 (C=C).

2-cyano-3-(1,4-dihydroxy-2-tetralyl)thioacrylamide

| $C_{14}H_{14}N_2O_2S$ | requires: | C 61.30 | H 5.14 | N 10.21 | S 11.69 |
|---|---|---|---|---|---|
| | found: | C 61.25 | H 5.01 | N 10.05 | S 11.65 |

MS m/z 274
IR $cm^{-1}$: 3100–3400 (NH,OH), 2200 (CN), 1620, 1570 (C=C).

2-cyano-3-(2-hydroxy-1-naphthyl)acrylonitrile

| $C_{14}H_8N_2O$ | requires: | C 76.33 | H 3.66 | N 12.72 |
|---|---|---|---|---|
| | found: | C 76.11 | H 3.71 | N 12.73 |

MS m/z 220
NMR δ ppm: 7.36 (d,1H), 7.5–7.9 (m,2H), 7.99 (d,1H), 8.17 (d,1H), 9.47 (d,1H), 8.79 (d,1H), 9.17 (d,1H).

2-cyano-3-(2-naphthyl)acrylamide

| $C_{14}H_{10}N_2O$ | requires: | C 75.66 | H 4.54 | N 12.60 |
|---|---|---|---|---|
| | found: | C 75.63 | H 4.51 | N 12.65 |

MS m/z 225
IR $cm^{-1}$: 3390 (NH), 3180 (NH), 2210 (CN), 1690 (CO), 1615 (amide), 1595, 1585 (arom).

2-cyano-3-(2-naphthyl)thioacrylamide

| $C_{14}H_{10}N_2S$ | requires: | C 70.56 | H 4.23 | N 11.76 | S 13.45 |
|---|---|---|---|---|---|
| | found: | C 69.12 | H 4.35 | N 11.98 | S 13.10 |

MS m/z 238
NMR δ ppm: 7.65 (2H,m), 8.05 (4H,m), 8.24 (1H,s), 8.44 (1H,s), 9.68, 10.15 (2H,bs).

2-cyano-3-(3,5-dihydroxy-2-naphthyl)acrylamide

| $C_{14}H_{10}N_2O_3$ | requires: | C 66.13 | H 3.97 | N 11.02 |
|---|---|---|---|---|
| | found: | C 66.98 | H 3.85 | N 10.72 |

MS m/z 254.

EXAMPLE 8

Tablets each weighing 0.150 g and containing 25 mg of the active substance, can be manufactured as follows: composition (for 10,000 tablets):

| | |
|---|---|
| 5-amino-3-[(8'-hydroxy-5'-quinolyl)methylene]-2-oxindole | 250 g |
| Lactose | 800 g |
| Corn starch | 415 g |
| Talc powder | 30 g |
| Magnesium stearate | 5 g |

The 5-amino-3-[(8'-hydroxy-5'-quinolyl)methylene]-2-oxindole, the lactose and half the corn starch are mixed; the mixture is then forced through a sieve of 0.5 mm mesh size.

Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

EXAMPLE 9

Capsules, each dosed at 0.200 g and containing 20 mg of the active substance can be prepared: composition for 500 capsules:

| | |
|---|---|
| 3-[(5'-methoxy-3'-indolyl)methylene]-2 oxindole | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

We claim:

1. A compound having the following general formula (I)

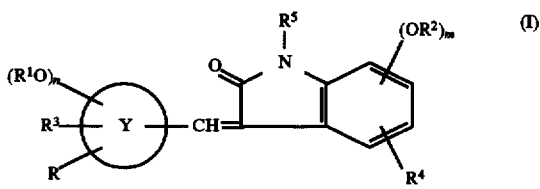

wherein

Y is a moiety selected from the group consisting of naphthyl, tetralyl, quinolyl and isoquinolyl;

R is hydrogen or an oxo (=O) group when Y is tetralin; or R is hydrogen when Y is naphthyl, quinolyl or isoquinolyl;

each of $R^1$ and $R^2$ independently is hydrogen, $C_1$–$C_6$ alkyl or $C_2$–$C_6$ alkanoyl;

m is zero, 1 or 2;

n is zero, 1, 2 or 3;

each of $R^1$ and $R^4$ independently is hydrogen, halogen, cyano, $C_1$–$C_6$ alkyl, carbon, nitro or —$NR^6R^7$ in which each of $R^6$ and $R^7$ independently is hydrogen or $C_1$–$C_6$ alkyl;

$R^5$ is hydrogen or $C_1$–$C_6$ alkyl; or a pharmaceutically acceptable salt thereof; with the provisos that a) when at the same time Y is naphthyl; $R^3$ is hydrogen, halogen, cyano or $C_1$–$C_6$ alkyl; $R^5$ is hydrogen; m is zero and n, R and $R^1$ are as defined above, then $R^4$ is other than hydrogen;

b) when at the same time Y is quinolyl or isoquinolyl; $R_3$ is hydrogen, halogen, cyano or $C_1$–$C_6$ alkyl; n is zero, 1 or 2; $R^5$ is hydrogen; m is zero and R and $R^1$ are as defined above, then $R^4$ is other than hydrogen;

c) when at the same time Y is tetralyl in which only the benzene moiety is substituted, $R^3$ is hydrogen, halogen, cyano or $C_1$–$C_6$ alkyl; n is zero, 1 or 2; $R^5$ is hydrogen; m is zero, R is hydrogen and $R^1$ is as defined above, then $R^4$ is other than hydrogen;

and d) when at the same time Y is naphthyl; m and n are zero; R and $R^3$ are hydrogen; $R^4$ being linked at the C-4 carbon atom is halogen or $C_1$–$C_4$ alkyl, then $R^5$ is other than $C_1$–$C_2$ alkyl.

2. The compound of claim 1,
wherein

Y is tetralyl, quinolyl or isoquinolyl;

n is zero, 1, 2 or 3;

m is zero or 1;

each of $R^1$ and $R^2$ independently is hydrogen or $C_1$–$C_4$ alkyl;

each of $R^3$ and $R^4$ independently is hydrogen, halogen, cyano, carboxy or amino;

$R^5$ is hydrogen; and

R is defined in claim 1; or a pharmaceutically acceptable salt thereof.

3. The compound of claim 1,
wherein,

Y is tetralyl or quinolyl;

n is zero, 1, 2 or 3;

m is zero or 1;

$R^1$, $R^2$ and $R^5$ are hydrogen;

each of $R^3$ and $R^4$ independently is hydrogen, amino or carboxy; and

R is as defined in claim 1, or a pharmaceutically acceptable salt thereof.

4. A compound selected from

3-[(4'-amino-1'-tetralyl)methylene]-2-oxindole;

3-[(4'-dimethylamino-1'-tetralyl)methylene]-2-oxindole;

3-[(4'-carboxy-1'-tetralyl)methylene]-2-oxindole;

5-hydroxy-3-[(1'-tetralyl)methylene]-2-oxindole;

5-amino-3-[(1'-tetralyl)methylene]-2-oxindole;

5-carboxy-3-[(1'-tetralyl)methylene]-2-oxindole;

5-hydroxy-3-[(2'-hydroxy-1'-tetralyl)methylene]-2-oxindole;

5-hydroxy-3-[(4'-hydroxy-1'-tetralyl)methylene]-2-oxindole;

5-amino-3-[(2'-hydroxy-1'-tetralyl)methylene]-2-oxindole;

5-amino-3-[(4'-hydroxy-1'-tetralyl)methylene]-2-oxindole;

5-carboxy-3-[(2'-hydroxy-1'-tetralyl)methylene]-2-oxindole;

5-carboxy-3-[(4'-hydroxy-1'-tetralyl)methylene]-2-oxindole;

5-hydroxy-3-[(4',5'-dihydroxy-1'-tetralyl)methylene]-2-oxindole;

5-hydroxy-3-[(4',8'-dihydroxy-1'-tetralyl)methylene]-2-oxindole;

5-amino-3-[(4',5'-dihydroxy-1'-tetralyl)methylene]-2-oxindole;

5-amino-3-[(4',5'-dihydroxy-1'-tetralyl)methylene]-2-oxindole;

5-carboxy-3-[(4',5'-dihydroxy-1'-tetralyl)methylene]-2-oxindole;

3-[(4'-amino-2'-tetralyl)methylene]-2-oxindole;

3-[(4'-carboxy-2'-tetralyl)methylene]-2-oxindole;

5-hydroxy-3-[(2'-tetralyl)methylene]-2-oxindole;

5-amino-3-[(2'-tetralyl)methylene]-2-oxindole;

5-carboxy-3-[(2'-tetralyl)methylene]-2-oxindole;

5-hydroxy-3-[(1'-hydroxy-2'-tetralyl)methylene]-2-oxindole;

5-hydroxy-3-[(3'-hydroxy-2'-tetralyl)methylene]-2-oxindole;

5-hydroxy-3-[(4'-hydroxy-2'-tetralyl)methylene]-2-oxindole;

5-amino-3-[(1'-hydroxy-2'-tetralyl)methylene]-2-oxindole 5-amino-3-[(3'-hydroxy-2'-tetralyl)methylene]-2-oxindole;

5-amino-3-[(4'-hydroxy-2'-tetralyl)methylene]-2-oxindole;

5-carboxy-3-[(1'-hydroxy-2'-tetralyl)methylene]-2-oxindole;

5-carboxy-3-[(3'-hydroxy-2'-tetralyl)methylene]-2-oxindole;

5-carboxy-3-[(4'-hydroxy-2'-tetralyl)methylene]-2-oxindole;

5-hydroxy-3-[(1',4'-dihydroxy-2'-tetralyl)methylene]-2-oxindole;

5-hydroxy-3-[(4',5'-dihydroxy-2'-tetralyl)methylene]-2-oxindole;

5-hydroxy-3-[(4',8'-dihydroxy-2'-tetralyl)methylene]-2-oxindole;

5-hydroxy-3-[(3',5'-dihydroxy-2'-tetralyl)methylene]-2-oxindole;

5-hydroxy-3-[(3',8'-dihydroxy-2'-tetralyl)methylene]-2oxindole;

5-amino-3-[(1',4'-dihydroxy-2'-tetralyl)methylene]-2-oxindole;

5-amino-3-[(4',5'-dihydroxy-2'-tetralyl)methylene]-2-oxindole;

5-amino-3-[(4',8'-dihydroxy-2'-tetralyl)methylene]-2-oxindole;

5-amino-3-[(3',5'-dihydroxy-2'-tetralyl)methylene]-2-oxindole;

5-amino-3-[(3',8'-dihydroxy-2'-tetralyl)methylene]-2-oxindole;

5-carboxy-3-[(1',4'-dihydroxy-2'-tetralyl)methylene]-2-oxindole;

5-carboxy-3-[(4',5'-dihydroxy-2'-tetralyl)methylene]-2-oxindole;

5-carboxy-3-[(4',8'-dihydroxy-2'-tetralyl)methylene]-2-oxindole;

5-carboxy-3-[(3',5'-dihydroxy-2'-tetralyl)methylene]-2-oxindole;

5-carboxy-3-[(3',8'-dihydroxy-2'-tetralyl)methylene]-2-oxindole;

5-hydroxy-3-[(1',4',5'-trihydroxy-2'-tetralyl)methylene]-2-oxindole;

5-hydroxy-3-[(1',4',8'-trihydroxy-2'-tetralyl)methylene]-2-oxindole;

3-[(8'-oxo-1',4'-dihydroxy-2'-tetralyl)methylene]-2-oxindole;

5-hydroxy-3-[(5'-quinolyl)methylene]-2-oxindole;

5-amino-3-[(5'-quinolyl)methylene]-2-oxindole;

5-carboxy-3-[(5'-quinolyl)methylene]-2-oxindole;

5-hydroxy-3-[(4'-quinolyl)methylene]-2-oxindole;

5-amino-3-[(4'-quinolyl)methylene]-2-oxindole;

5-carboxy-3-[(4'-quinolyl)methylene]-2-oxindole;

5-hydroxy-3-[(8'-hydroxy-5'-quinolyl)methylene]-2-oxindole;

5-amino-3-[(8'-hydroxy-5'-quinolyl)methylene]-2-oxindole;

5-carboxy-3-[(8'-hydroxy-5'-quinolyl)methylene]-2-oxindole;

5-hydroxy-3-[(8'-hydroxy-4'-quinolyl)methylene]-2-oxindole;

5-amino-3-[(8'-hydroxy-4'-quinolyl)methylene]-2-oxindole;

5-carboxy-3-[(8'-hydroxy-4'-quinolyl)methylene]-2-oxindole;

5-bromo-3-[(8'-hydroxy-5'-quinolyl)methylene]-2-oxindole;

5-fluoro-3-[(8'-hydroxy-5'-quinolyl)methylene]-2-oxindole;

5-methoxy-3-[(2'-tetralyl)methylene]-2-oxindole;

5-acethoxy-3-[(2'-tetralyl)methylene]-2-oxindole;

5-hydroxy-3-[(4'-hydroxy-1'-tetralyl)methylene]-2-oxindole;

pharmaceutically acceptable salt thereof.

5. A compound selected from:

3-[(8'-hydroxy-7'-quinolyl)methylene]-2-oxindole;

3-[(5'-hydroxy-4'-quinolyl)methylene]-2-oxindole;

3-[(8'-hydroxy-4'-quinolyl)methylene]-2-oxindole;

5-hydroxy-3-[(5'-methoxy-3'-indolyl)methylene]-2-oxindole;

5-amino-3-[(5'-methoxy-3'-indolyl)methylene]-2-oxindole;

5-hydroxy-3-[(2'-methyl-3'-indolyl)methylene]-2-oxindole;

3-[(2'-methyl-3'-indolyl)methylene]-2-oxindole;

3-[(5'-cyano-3'-indolyl)methylene]-2-oxindole;

3-[(5'-hydroxy-3'-indolyl)methylene]-2-oxindole; and

3-[(5'-methoxy-3'-indolyl)methylene]-2-oxindole, or a pharmaceutically acceptable salt thereof.

6. The compound of claim 1, wherein Y is quinolyl.

7. The compound of claim 2, wherein Y is quinolyl.

8. The compound of claim 3, wherein Y is quinolyl.

9. A compound selected from the group consisting of 5-hydroxy-3-[(5'-quinolyl)methylene]-2-oxindole;

5-amino-3-[(5'-quinolyl)methylene]-2-oxindole;

5-carboxy-3-[(5'-quinolyl)methylene]-2-oxindole;

5-hydroxy-3-[(4'-quinolyl)methylene]-2-oxindole;

5-amino-3-[(4'-quinolyl)methylene]-2-oxindole;

5-carboxy-3-[(4'-quinolyl)methylene]-2-oxindole;

5-hydroxy-3-[(8'-hydroxy-5'-quinolyl)methylene]-2-oxindole;

5-amino-3-[(8'-hydroxy-5'-quinolyl)methylene]-2-oxindole;

5-carboxy-3-[(8'-hydroxy-5'-quinolyl)methylene]-2-oxindole;

5-hydroxy-3-[(8'-hydroxy-4'-quinolyl)methylene]-2-oxindole;

5-amino-3-[(8'-hydroxy-4'-quinolyl)methylene]-2-oxindole;

5-carboxy-3-[(8'-hydroxy-4'-quinolyl)methylene]-2-oxindole;

5-bromo-3-[(8'-hydroxy-5'-quinolyl)methylene]-2-oxindole; and 5-fluoro-3-[(8'-hydroxy-5'-quinolyl)methylene]-2-oxindole;

or a pharmaceutically acceptable salt thereof.

10. A compound selected from the group consisting of:

3-[(8'-hydroxy-7'-quinolyl)methylene]-2-oxindole;

3-[(5'-hydroxy-4'-quinolyl)methylene]-2-oxindole; and

3-[(8'-hydroxy-4'-quinolyl)methylene]-2-oxindole;

or a pharmaceutically acceptable salt thereof.

11. The compound according to claim 1, which is 5-bromo-3-[(8'-hydroxy-5'-quinolyl)methylene]-2-oxindole.

12. A pharmaceutical composition containing a suitable carrier and/or diluent and, as an active principle, a compound of formula (I) according to claim 1 or a pharmaceutically acceptable salt thereof.

13. A method of inhibiting tyrosine kinase in a patient in need thereof, the method comprising administering to said patient a therapeutically effective amount of a compound of formula (I)

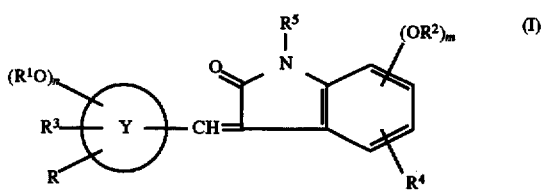

wherein
Y is a a moiety selected from the group consisting of naphthyl, tetralyl, quinolyl and isoquinolyl;
R is hydrogen or an oxo (=O) group when Y is tetralyl, or R is hydrogen when Y is naphthyl, quinolyl or isoquinolyl;
each of $R^1$ and $R^2$ independently is hydrogen $C_1$–$C_6$ alkyl or $C_2$–$C_6$ alkanoyl;
m is zero, 1 or 2;
n is zero, 1, 2 or 3;
each of $R^3$ and $R^4$ independently is hydrogen, halogen, cyano, $C_1$–$C_6$ alkyl, carboxy, nitro or —$NR^6R^7$ in which each of $R^6$ and $R^7$ independently is hydrogen or $C_1$–$C_6$ alkyl;
$R^5$ is hydrogen or $C_1$–$C_6$ alkyl; or a pharmaceutically acceptable salt thereof; and wherein
a) when at the same time Y is naphthyl; $R^3$ is hydrogen, halogen, cyano or $C_1$–$C_6$ alkyl; $R^5$ is hydrogen; m is zero and n, R and $R^1$ are as defined above, then $R^4$ is other than hydrogen;
b) when at the same time Y is quinolyl or isoquinolyl; $R^3$ is hydrogen, halogen, cyano or $C_1$–$C_6$ alkyl; n is zero, 1 or 2; $R^5$ is hydrogen; m is zero and R and $R^1$ are as defined above, then $R^4$ is other than hydrogen; and
c) when at the same time Y is tetralyl in which only the benzene moiety is substituted, $R^3$ is hydrogen, halogen, cyano or $C_1$–$C_6$ alkyl; n is zero, 1 or 2; $R^5$ is hydrogen; m is zero, R is hydrogen and $R^1$ is as defined above, then $R^4$ is other than hydrogen; or a pharmaceutically acceptable salt thereof.

14. A method of treating a pathological proliferative disorder comprising administering to a patient a therapeutically effective amount of a compound of formula (I)

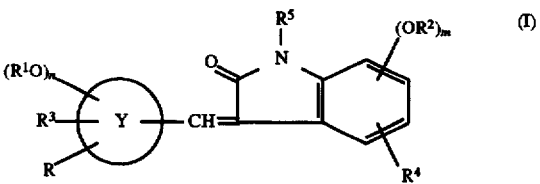

wherein
Y is a moiety selected from the group consisting of naphthyl, tetralyl, quinolyl and isoquinolyl;
R is hydrogen or an oxo (=O) group when Y is tetralin; or R is hydrogen when Y is naphthyl, quinolyl or isoquinolyl;
each of $R^1$ and $R^2$ independently is hydrogen, $C_1$–$C_6$ alkyl or $C_2$–$C_6$ alkanoyl;
m is zero, 1 or 2;
n is zero, 1, 2 or 3;
each of $R^3$ and $R^4$ independently is hydrogen, halogen, cyano, $C_1$–$C_6$ alkyl, carboxy, nitro or —$NR^6R^7$ in which each of $R^6$ and $R^7$ independently is hydrogen or $C_1$–$C_6$ alkyl;

$R^5$ is hydrogen or $C_1$–$C_6$ alkyl; or a pharmaceutically acceptable salt thereof; with the provisos that
a) when at the same time Y is naphthyl; $R^3$ is hydrogen, halogen, cyano or $C_1$–$C_6$ alkyl; $R^5$ is hydrogen; m is zero and n, R and $R^1$ are as defined above, then $R^4$ is other than hydrogen;
b) when at the same time Y is quinolyl or isoquinolyl; $R_3$ is hydrogen, halogen, cyano or $C_1$–$C_6$ alkyl; n is zero, 1 or 2; $R^5$ is hydrogen; m is zero and R and $R^1$ are as defined above, then $R^4$ is other than hydrogen; and
c) when at the same time Y is tetralyl in which only the benzene moiety is substituted, $R^3$ is hydrogen, halogen, cyano or $C_1$–$C_6$ alkyl; n is zero, 1 or 2; $R^5$ is hydrogen; m is zero, R is hydrogen and $R^1$ is as defined above, then $R^4$ is other than hydrogen.

15. A method of treating a pathological proliferative disorder comprising administering to a patient a therapeutically effective amount of a compound selected from the group consisting of
3-((8'-hydroxy-7'-quinolyl)methylene)-2-oxindole;
3-((5'-hydroxy-4'-quinolyl)methylene)-2-oxindole;
3-((8'-hydroxy-4'-quinolyl)methylene)-2-oxindole;
5-hydroxy-3-((5'-methoxy-3'-indolyl)methylene)-2-oxindole;
5-amino-3-((5'-methoxy-3'-indolyl)methylene)-2-oxindole;
5-hydroxy-3-((2'-methyl-3'-indolyl)methylene)-2-oxindole;
3-((2'-methyl-3'-indolyl)methylene)-2-oxindole;
3-((5'-cyano-3'-indolyl)methylene)-2-oxindole;
3-((5'-hydroxy-3'-indolyl)methylene)-2-oxindole;
3-((5'-methoxy-3'-indolyl)methylene)-2-oxindole;
or a pharmaceutically acceptable salt thereof.

16. A process for the preparation of a compound of formula (I) according to claim 1 or a pharmaceutically acceptable salt thereof, the process comprising condensing an aldehyde of formula (II)

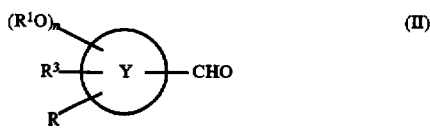

wherein Y, n, R, $R^1$ and $R^3$ are as defined in claim 1, with a compound of formula (III)

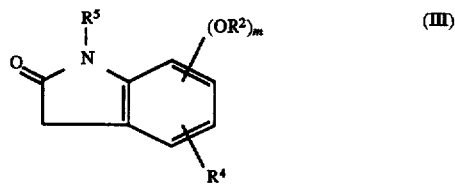

wherein, m, $R^2$, $R^4$ and $R^5$ are as defined in claim 1.

17. The process of claim 16, which further comprises: salifying a compound of formula (I) to form a pharmaceutically acceptable salt thereof.

18. The process of claim 16, which further comprises separating a mixture of isomers of a compound of formula (I) into single isomers.

* * * * *

UNITED STATES PATENT AND TRADEMARK OFFICE
CERTIFICATE OF CORRECTION

PATENT NO. : 5,656,654
DATED : Aug. 12, 1997
INVENTOR(S) : Buzzetti, et al.

It is certified that error appears in the above-identified patent and that said Letters Patent is hereby corrected as shown below:

Please delete columns 1-30 and substitute columns 1-24 as per attached.

Signed and Sealed this

Sixteenth Day of December, 1997

*Attest:*

BRUCE LEHMAN

*Attesting Officer*  *Commissioner of Patents and Trademarks*

ARYLIDENE AND HETEROARYLIDENE OXINDOLE DERIVATIVES AND PROCESS FOR THEIR PREPARATION

The present invention relates to new 3-arylidene and 3-heteroarylidene-2-oxindole derivatives, to a process for their preparation, to pharmaceutical compositions containing them and to their use as therapeutic agents. The present invention provides compounds having the following general formula (I)

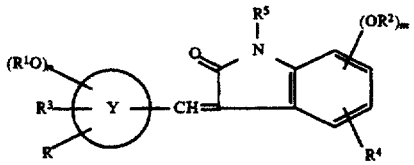

wherein

Y is a bicyclic ring system chosen from naphthalene, tetralin, quinoline and isoquinoline;

R is hydrogen or an oxo (=O) group when Y is tetralin, or R is hydrogen when Y is naphthalene, quinoline or isoquinoline;

each of $R^1$ and $R^2$ independently is hydrogen, $C_1$–$C_6$ alkyl or $C_2$–$C_6$ alkanoyl;

m is zero, 1 or 2;

n is zero, 1, 2 or 3;

each of $R^3$ and $R^4$ independently is hydrogen, halogen, cyano, $C_1$–$C_6$ alkyl, carboxy, nitro or —$NR^6R^7$ in which each of $R^6$ and $R^7$ independently is hydrogen or $C_1$–$C_6$ alkyl;

$R^5$ is hydrogen or $C_1$–$C_6$ alkyl; and the pharmaceutically acceptable salts thereof; and wherein a) when at the same time Y is naphthalene; $R^3$ is hydrogen, halogen, cyano or $C_1$–$C_6$ alkyl; $R^5$ is hydrogen; m is zero and n, R and $R^1$ are as defined above, then $R^4$ is other than hydrogen;

b) when at the same time Y is quinoline or isoquinoline; $R_3$ is hydrogen, halogen, cyano or $C_1$–$C_6$ alkyl; n is zero, 1 or 2; $R^5$ is hydrogen; m is zero and R and $R^1$ are as defined above, then $R^4$ is other than hydrogen;

c) when at the same time Y is tetralin in which only the benzene moiety is substituted, $R^3$ is hydrogen, halogen, cyano or $C_1$–$C_6$ alkyl; n is zero, 1 or 2; $R^5$ is hydrogen; m is zero, R is hydrogen and $R^1$ is as defined above, then $R^4$ is other than hydrogen; and d) when at the same time Y is naphthalene; m and n are zero; R and $R^3$ are hydrogen; $R^4$ being linked at the C-4 carbon atom is halogen or $C_1$–$C_4$ alkyl, then $R^5$ is other than $C_1$–$C_2$ alkyl.

The invention includes within its scope all the possible isomers, stereoisomers, in particular Z and E isomers and their mixtures, and the metabolites and the metabolic precursors or bio-precursors (otherwise known as pro-drugs) of the compounds of formula (I).

The alkyl group, and the alkyl moiety in the alkanoyl groups, may be branched or straight alkyl chain. A $C_1$–$C_6$ alkyl group is preferably a $C_1$–$C_4$ alkyl group, e.g. methyl, ethyl, propyl, isopropyl, butyl, sec-butyl or tert-butyl, in particular methyl or ethyl. A $C_2$–$C_6$ alkanoyl group is preferably a $C_2$–$C_4$ alkanoyl group, in particular acetyl, propionyl or butyryl.

A halogen is preferably fluorine, chlorine or bromine, in particular fluorine or chlorine.

The term tetralin preferably is meant to refer to a 5,6,7,8-tetrahydronaphthalene ring system.

When the R oxo (=O) group is a substituent on the tetralin ring, said oxo group can be attached only to the saturated moiety of the tetralin ring, thus providing a 5-, 6-, 7- or 8-tetralone ring system, preferably 8-tetralone.

When Y is tetralin preferably the oxindolylidene substituent is on the benzene moiety whereas the $R^3$ and the $R^1$O-group(s) may be on either of the rings.

When tetralin is substituted at the position 1' by the oxindolylidene substituent, preferably at least one —$OR^1$ group is present at the positions 2', 4', 5' and/or 8' and preferably the $R^3$ substituent is at the 4' position.

Analogously when tetralin is substituted at the 2'-position by the oxindolylidene substituent, preferably at least one —$OR^1$ group is present at the positions 1', 3', 4', 5' and/or 8' and the $R^3$ substituent is preferably at the 4'-position.

When Y is naphthalene the $R^3$, the $R^1$O-group(s) and the oxindolylidene substituents are preferably on the same benzene moiety.

When Y is quinoline the oxindolylidene group is preferably attached to the 4'- or 5'-position of the quinoline ring whereas the $R^3$ and $R^1$O substituents may be on either of the rings of said ring system.

When Y is isoquinoline the oxindolylidene group is preferably attached to the 3'- or 5'-position of the isoquinoline ring whereas the $R^3$ and $R^1$O substituent(s) may be on either of ring moieties.

When Y is quinoline, it is preferably substituted at the positions 4' or 5' by the oxindolylidene substituent and at least one OR' substituent is present, preferably at the 8' position.

Preferably at least one of the substituents $R^4$ or —$OR^2$ is present on the 2-oxindole ring. Preferred substitution positions are the positions 4 and 5, in particular position 5.

When $R^4$ is carboxy, nitro or —$NR^6R^7$ in which $R^6$ and $R^7$ are as defined above, the $R^3$ substituent is preferably other than carboxy, nitro or —$NR^6R^7$. Vice versa, when $R^3$ is carboxy, nitro or —$NR^6R^7$ in which $R^6$ and $R^7$ are as defined above, the $R^4$ substituent preferably is other than carboxy, nitro or —$NR^6R^7$.

Of course only one of the substituents $R^1$O, $R^2$O, $R^3$, R and $R^4$ can be linked to the same ring position.

Pharmaceutically acceptable salts of the compounds of the invention include acid addition salts, with inorganic, e.g. nitric, hydrochloric, hydrobromic, sulphuric, perchloric and phosphoric acids, or organic, e.g. acetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium, bases or alkaline-earth metal, especially calcium or magnesium bases, or with organic bases, e.g. alkylamines, preferably triethylamine.

As stated above, the present invention also includes within its scope pharmaceutically acceptable bioprecursors (otherwise known as pro-drugs) of the compounds of formula (I), i.e. compounds which have a different formula to formula (I) above, but which nevertheless upon administration to human being are converted directly or indirectly in vivo into a compound of formula (I).

Preferred compounds of the invention are the compounds of formula (I), wherein subject to the above provisos, Y is tetralin, quinoline or isoquinoline;

n is zero, 1, 2 or 3;

m is zero or 1;

each of $R^1$ and $R^2$ independently is hydrogen or $C_1$–$C_4$ alkyl;

each of $R^3$ and $R^4$ independently is hydrogen, halogen, cyano, carboxy or amino;

$R^5$ is hydrogen;

R is defined above; and the pharmaceutically acceptable salts thereof.

More preferred compounds of the invention are the compounds of formula (I), wherein subject to the above provisos, Y is tetralin or quinoline;
n is zero, 1, 2 or 3;
m is zero or 1;
$R^1$, $R^2$ and $R^5$ are hydrogen;
each of $R^3$ and $R^4$ independently is hydrogen, amino or carboxy;
R is as defined above; and the pharmaceutically acceptable salts thereof.

Examples of specific compounds of the invention are the following compounds, which, when appropriate, may be either Z- or E-diastereoisomers or Z, E-mixtures of said diastereoisomers.

3-[(4'-amino-1'-tetralyl)methylene]-2-oxindole;
3-[(4'-dimethylamino-1'-tetralyl)methylene]-2-oxindole;
3-[(4'-carboxy-1'-tetralyl)methylene]-2-oxindole;
5-hydroxy-3-[(1'-tetralyl)methylene]-2-oxindole;
5-amino-3-[(1'-tetralyl)methylene]-2-oxindole;
5-carboxy-3-[(1'-tetralyl)methylene]-2-oxindole;
5-hydroxy-3-[(2'-hydroxy-1'-tetralyl)methylene]-2-oxindole;
5-hydroxy-3-[(4'-hydroxy-1'-tetralyl)methylene]-2-oxindole;
5-amino-3-[(2'-hydroxy-1'-tetralyl)methylene]-2-oxindole;
5-amino-3-[(4'-hydroxy-1'-tetralyl)methylene]-2-oxindole;
5-carboxy-3-[(2'-hydroxy-1'-tetralyl)methylene]-2-oxindole;
5-carboxy-3-[(4'-hydroxy-1'-tetralyl)methylene]-2-oxindole;
5-hydroxy-3-[(4',5'-dihydroxy-1'-tetralyl)methylene]-2-oxindole;
5-hydroxy-3-[(4',8'-dihydroxy-1'-tetralyl)methylene]-2-oxindole;
5-amino-3-[(4',5'-dihydroxy-1'-tetralyl)methylene]-2-oxindole;
5-amino-3-[(4',8'-dihydroxy-1'-tetralyl)methylene]-2-oxindole;
5-carboxy-3-[(4',5'-dihydroxy-1'-tetralyl)methylene]-2-oxindole;
3-[(4'-amino-2'-tetralyl)methylene]-2-oxindole;
3-[(4'-carboxy-2'-tetralyl)methylene]-2-oxindole;
5-hydroxy-3-[(2'-tetralyl)methylene]-2-oxindole;
5-amino-3-[(2'-tetralyl)methylene]-2-oxindole;
5-carboxy-3-[(2'-tetralyl)methylene]-2-oxindole;
5-hydroxy-3-[(1'-hydroxy-2'-tetralyl)methylene]-2-oxindole;
5-hydroxy-3-[(3'-hydroxy-2'-tetralyl)methylene]-2-oxindole;
5-hydroxy-3-[(4'-hydroxy-2'-tetralyl)methylene]-2-oxindole;
5-amino-3-[(1'-hydroxy-2'-tetralyl)methylene]-2-oxindole;
5-amino-3-[(3'-hydroxy-2'-tetralyl)methylene]-2-oxindole;
5-amino-3-[(4'-hydroxy-2'-tetralyl)methylene]-2-oxindole;
5-carboxy-3-[(1'-hydroxy-2'-tetralyl)methylene]-2-oxindole;
5-carboxy-3-[(3'-hydroxy-2'-tetralyl)methylene]-2-oxindole;
5-carboxy-3-[(4'-hydroxy-2'-tetralyl)methylene]-2-oxindole;
5-hydroxy-3-[(1',4'-dihydroxy-2'-tetralyl)methylene]-2-oxindole;
5-hydroxy-3-[(4',5'-dihydroxy-2'-tetralyl)methylene]-2-oxindole;
5-hydroxy-3-[(4',8'-dihydroxy-2'-tetralyl)methylene]-2-oxindole;
5-hydroxy-3-[(3',5'-dihydroxy-2'-tetralyl)methylene]-2-oxindole;
5-hydroxy-3-[(3',8'-dihydroxy-2'-tetralyl)methylene]-2-oxindole;
5-amino-3-[(1',4'-dihydroxy-2'-tetralyl)methylene]-2-oxindole;
5-amino-3-[(4',5'-dihydroxy-2'-tetralyl)methylene]-2-oxindole;
5-amino-3-[(4',8'-dihydroxy-2'-tetralyl)methylene]-2-oxindole;
5-amino-3-[(3',5'-dihydroxy-2'-tetralyl)methylene]-2-oxindole;
5-amino-3-[(3',8'-dihydroxy-2'-tetralyl)methylene]-2-oxindole;
5-carboxy-3-[(1',4'-dihydroxy-2'-tetralyl)methylene]-2-oxindole;
5-carboxy-3-[(4',5'-dihydroxy-2'-tetralyl)methylene]-2-oxindole;
5-carboxy-3-[(4',8'-dihydroxy-2'-tetralyl)methylene]-2-oxindole;
5-carboxy-3-[(3',5'-dihydroxy-2'-tetralyl)methylene]-2-oxindole;
5-carboxy-3-[(3',8'-dihydroxy-2'-tetralyl)methylene]-2-oxindole;
5-hydroxy-3-[(1',4',5'-trihydroxy-2'-tetralyl)methylene]-2-oxindole;
5-hydroxy-3-[(1',4',8'-trihydroxy-2'-tetralyl)methylene]-2-oxindole;
3-[(8'-oxo-1',4'-dihydroxy-2'-tetralyl)methylene]-2-oxindole;
5-hydroxy-3-[(5'-quinolyl)methylene]-2-oxindole;
5-amino-3-[(5'-quinolyl)methylene]-2-oxindole;
5-carboxy-3-[(5'-quinolyl)methylene]-2-oxindole;
5-hydroxy-3-[(4'-quinolyl)methylene]-2-oxindole;
5-amino-3-[(4'-quinolyl)methylene]-2-oxindole;
5-carboxy-3-[(4'-quinolyl)methylene]-2-oxindole;
5-hydroxy-3-[(8'-hydroxy-5'-quinolyl)methylene]-2-oxindole;
5-amino-3-[(8'-hydroxy-5'-quinolyl)methylene]-2-oxindole;
5-carboxy-3-[(8'-hydroxy-5'-quinolyl)methylene]-2-oxindole;
5-hydroxy-3-[(8'-hydroxy-4'-quinolyl)methylene]-2-oxindole;
5-amino-3-[(8'-hydroxy-4'-quinolyl)methylene]-2-oxindole; and
5-carboxy-3-[(8'-hydroxy-4'-quinolyl)methylene]-2-oxindole;
5-bromo-3-[(8'-hydroxy-5'-quinolyl)methylene]-2-oxindole;

5-fluoro-3-[(8'-hydroxy-5'-quinolyl)methylene]-2-oxindole;

5-methoxy-3-[(2'-tetralyl)methylene]-2-oxindole;

5-acethoxy-3-[(2'-tetralyl)methylene]-2-oxindole;

5-hydroxy-3-[(4'-hydroxy-1'-tetralyl)methylene]-2-oxindole;

and if the case the pharmaceutically acceptable salts thereof.

A further object of the present invention are the following compounds and the pharmaceutically acceptable salts thereof, which are new and are encompassed by the chemical general formula disclosed by WO 91/13055 and WO 93/01182, but therein not disclosed as specific chemical entities:

3-[(8'-hydroxy-7'-quinolyl)methylene]-2-oxindole;

3-[(5'-hydroxy-4'-quinolyl)methylene]-2-oxindole;

3-[(8'-hydroxy-4'-quinolyl)methylene]-2-oxindole;

3-[(2'-methyl-3'-indolyl)methylene]-2-oxindole;

3-[(5'-cyano-3'-indolyl)methylene]-2-oxindole;

3-[(5'-hydroxy-3'-indolyl)methylene]-2-oxindole;

3-[(5'-methoxy-3'-indolyl)methylene]-2-oxindole;

5-hydroxy-3-[(5'-methoxy-3'-indolyl)methylene]-2-oxindole;

5-amino-3-[(5'-methoxy-3'-indolyl)methylene]-2-oxindole;

5-hydroxy-3-[(2'-methyl-3'-indolyl)methylene]-2-oxindole;

2-cyano-3-(4-quinolyl)acrylamide;

2-cyano-3-(3-indolyl)acrylamide;

2-cyano-3-(1,4-dihydroxy-2-tetralyl)acrylamide;

2-cyano-3-(1,4-dihydroxy-2-tetralyl)thioacrylamide;

2-cyano-3-(2-hydroxy-1-naphthyl)acrylonitrile;

2-cyano-3-(2-naphthyl)acrylamide;

2-cyano-3-(2-naphthyl)thioacrylamide;

2-cyano-3-(3,5-dihydroxy-2-naphthyl)acrylamide; and 2-(4-hydroxyphenyl)-3-(1,4-dimethoxy-2-naphthyl)acrylonitrile;

which when appropriate may be either Z- or E-diastereoisomers or Z, E-mixtures thereof.

The compounds of formula (I), as defined above, and the pharmaceutically acceptable salts thereof can be obtained by a process comprising the condensation of an aldehyde of formula (II)

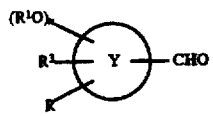

(II)

wherein Y, n, R, R$^1$ and R$^3$ are as defined above, with a compound of formula (III)

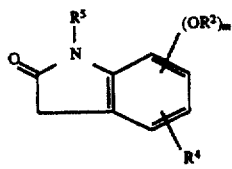

(III)

wherein, m, R$^2$, R$^4$ and R$^5$ are as defined above; and if desired, converting a compound of formula (I) into another compound of formula (I), and/or, if desired, converting a compound of formula (I) into a pharmaceutically acceptable salt thereof, and/or, if desired, converting a salt into a free compound, and/or, if desired, separating a mixture of isomers of a compound of formula (I) into the single isomers.

Each of the substituents —OR$^1$, R$^3$ and —CHO in a compound of formula (II) may be independently on either of the ring moieties of the bicyclic ring systems.

The condensation of a compound of formula (II) with a compound of formula (III) may be carried out according to known methods as herebelow described. For example it may be carried out under the conditions of the Knoevanagel reaction as described, e.g., by G. Jones in Organic Reactions 15, 204(1967). Suitable catalysts are organic bases such as pyridine, piperidine or diethylamine. The condensation may be performed in an inert organic solvent, e.g., pyridine, ethanol, methanol, benzene or dioxane at temperatures ranging from about 0° C. to about 100° C. Preferably the reaction is carried out in hot ethanol solution in the presence of piperidine catalyst.

A compound of formula (I) can be converted into another compound of formula (I) according to known methods. For example the de-etherification of a compound of formula (I) wherein one or more —OR$^1$ and/or —OR$^2$ methoxy groups are present to obtain the corresponding hydroxy substituted derivative can be carried out for example with boron tribromide as described by J. F. N. McOmie in Tetrahedron 24, 2289 (1968). The reaction may be performed in an inert organic solvent such as dichloromethane or benzene under an inert atmosphere (e.g. nitrogen) at temperatures ranging from about –78° C. to about room temperature.

The conversion of a compound of formula (I) in which R$^3$ and/or R$^4$ is nitro into the corresponding compound of formula (I), wherein R$^3$ and/or R$^4$ is amino, may be carried out following known methods, for example with a variety of reducing agents, e.g. sodium sulfide in hydroalcoholic solution, metallic iron with ammonium chloride in aqueous solvent, or for instance, catalytic hydrogenation using e.g. palladium charcoal catalyst at low hydrogen pressure in an inert organic solvent.

The alkylation of a compound of formula (I), wherein —OR$^1$ and/or —OR$^2$ is hydroxy, so as to obtain the corresponding compound of formula (I), wherein —OR$^1$ and/or —OR$^2$ is C$_1$–C$_6$ alkoxy, may be obtained, e.g., by reaction with sodium hydride and C$_1$–C$_6$ alkyl iodide in a high boiling aromatic solvent such as xylene.

The acylation of a compound of formula (I), wherein —OR$^1$ and/or —OR$^2$ is hydroxy, in order to obtain the corresponding compound of formula (I), wherein —OR$^1$ and/or —OR$^2$ is a C$_1$–C$_6$ alkanoyloxy, can be performed, e.g., by reaction with a suitable carboxylic acid anhydride in the presence of a basic agent at temperatures ranging from room temperature to reflux temperatures.

The optional salification of a compound of formula (I) as well as the conversion of a salt into a free compound, and the separation of a mixture of isomers into the single isomers may be carried out by conventional methods. For example the separation of a mixture of geometric isomers, e.g. Z- and E-isomers, may be carried out by fractional crystallization from a suitable solvent or by chromatography, either column chromatography or HPLC.

The compounds of formula (II) may be obtained according to known methods from compounds of formula (IV)

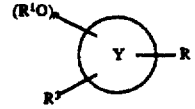

(IV)

wherein Y, R, n, R$^3$ and R$^1$ are as defined above.

For example when compound (IV) contains phenolic groups, i.e. R¹O— is hydroxy, the well known Reimer-Tiemann method can be applied. Thus the phenolic compound is treated with chloroform and alkali hydroxides in an aqueous or hydroalcoholic solution. Another useful method for the synthesis of aromatic or phenolic aldehydes has been described by H. Gross et al. in Chem. Ber. 96, 308 (1963). Accordingly a compound of formula (IV), in which the OR¹ group may be present or not, can be treated with a dichloromethyl ether, e.g. dichloromethyl methyl ether, in the presence of a Friedel-Crafts catalyst such as titanium tetrachloride or aluminium trichloride in an inert solvent like dichloromethane or nitrobenzene at temperatures ranging from about 0° C. to about 60° C.

The compounds of formula (III) and (IV) are known or may be obtained by known methods.

The new oxindolylidene derivatives and the pharmaceutically acceptable salts thereof, for the first time herein disclosed and encompassed by WO 91/13055 (U.S. Pat. No. 5,374,652) and WO 93/01182, (U.S. Pat. No. 5,409,944) can be obtained by following the same procedure described above for the preparation of a compound of formula (I). Of course a suitable quinoline- or indole-carboxaldehyde has to be chosen as will be easily appreciated by the skilled people in the art.

Similarly the novel acrylamide, thioacrylamide and acrylonitrile derivatives encompassed by the general formula (I) disclosed in WO 91/13055, and mentioned herein for the first time as specific chemical entities, can be obtained by following the procedures described in WO 91/13055 by reacting a suitable quinoline-, tetralin- or naphthalene-carboxaldehyde with cyanoacetamide, cyanothioacetamide or 4-hydroxybenzylcyanide, respectively. When in the new compounds of the present invention and in the intermediate products used for their preparation there are groups present which need to be protected before the above-described reactions are performed, they may be protected before the reaction takes place and then deprotected at the end of the reaction, according to well known methods in organic chemistry. The new compounds provided by the present invention, namely both the compounds of formula (I) as defined above and the new compounds herein specifically disclosed and encompassed by WO 91/13055 and WO 93/01182, are referred to as "the compounds of the invention".

Pharmacology

The compounds of the invention possess specific tyrosine kinase inhibiting activity. It is believed that tyrosine kinase inhibitors may be of great importance in the control of uncontrolled cellular reproduction, i.e. in cellular reproduction disorders. Hence the compounds according to the present invention can be useful in the treatment of pathological proliferation disorders in mammals, including humans.

A human or animal, e.g. a mammal, can thus be treated by a method comprising the administration thereto of a therapeutically effective amount of one of the compounds of the invention. In this way the condition of the human or animal may be improved. Amelioration of the disease state or disorder from which the human or animal is suffering can be achieved. Typical examples of such disorders are tumours, including leukaemia such as myeloblastic leukaemia, lymphoma, sarcoma, neuroblastoma, Wilm's tumour and malignant neoplasm of the bladder, breast, lung or thyroid; and psoriasis. The compounds of the invention can also be useful in inhibiting the development of the atheromatous plaque and in the control of angiogenesis and as antimetastatic agents.

Recent studies on the molecular basis or neoplastic transformation have identified a family of genes, designated oncogenes, whose aberrant expression causes tumorigenesis. For example, the RNA tumor viruses possess such an oncogene sequence whose expression determines neoplastic conversion of infected cells. Several of their oncogene-encoded proteins, such as pp60$^{v-src}$, p70$^{gag-yes}$, p130$^{gag-fps}$ and P70$^{gag-fer}$ display protein tyrosine kinase activity, that is they catalyse the transfer of the γ-phosphate from adenosine triphosphate (ATP) to tyrosine residues in protein substrate. In normal cells, several growth factor receptors, for example the receptors for PDGF, EGF, α-TGF and insulin, display tyrosine kinase activity.

Binding of the growth factor (GF) activates the receptor tyrosine kinase to undergo autophosphorylation and to phosphorylate closely adjacent molecules on tyrosine. Therefore, it is thought that the phosphorylation of these tyrosine kinase receptors plays an important role in signal transduction and that the principal function of tyrosine kinase activity in normal cells is to regulate cell growth. Perturbation of this activity by oncogenic tyrosine kinases that are either overproduced and/or display altered substrate specificity may cause loss of growth control and/or neoplastic transformation. Accordingly, a specific inhibitor of tyrosine kinase can be useful in investigating the mechanism of carcinogenesis, cell proliferation and differentiations and it can be effective in prevention and chemotherapy of cancer and in other pathological proliferative conditions, for instance as mentioned above. The tyrosine specific protein kinase activity of these compounds is shown e.g. by the fact that they are active in the following in vitro and in vivo tests described herebelow.

In Vitro ASSAY p45 v-abl kinase purification. The enzyme used in our test was the p45 v-abl tyrosine kinase which represents the catalytic domain of the Abelson tyrosine kinase (isolated from the Abelson murine leukemia virus). The p45 v-abl kinase was produced and isolated as described by Wang et al. in J. Biol. Chem. 260, 64 (1985) and by Ferguson et al. in J. Biol. Chem. 260, 3652 (1985) and in Biochem. J. 257, 321 (1989).

p45 v-abl Kinase Assay. (Val$^5$)-Angiotensin II phosphorylation was performed by incubation with 40 ng of purified abl-kinase and (γ-$^{32}$P)-ATP, in 50 μl of buffer containing Tris-HCl 25 mM, pH 8.0, MgCl$_2$ 10 mM and dithiothreitol 0.1 mM (kinase buffer). The reaction mixture was incubated for the indicated time at 30° C. and the reaction stopped by adding 50 μl of 5% trichloroacetic acid. After a brief incubation on ice, tubes were centrifuged. The supernatants were spotted on phosphocellulose paper squares (Whatman P-81) and washed extensively in acetic acid. The radioactivity bound to dried phosphocellulose squares was measured in a liquid scintillation counter. IC$_{50}$ values were calculated from triplicate determinations of each experimental point. Each inhibitor was tested at concentrations ranging from 0 to 400 μg in the presence of fixed concentrations of peptide (2 mM) and ATP (50 μM).

In Vivo ASSAY

K562 cell growth inhibition assay. 1 ml of K562 cells, grown in suspension, were incubated for 66 h with or without 10% foetal calf serum in the presence of 1 μCi of [$^3$-H]-Thymidine. Cells were harvested, washed three times in cold PBS and treated with 5% trichloroacetic acid for 5 min on ice. After a wash in ethanol: ether 2:1, the DNA was extracted by 0.5N NaOH for 2 h at room temperature. The extract was counted in a liquid scintillation counter.

The inhibitory activity data for a representative group of compounds according to the present invention, obtained both in the in vitro p45 v-abl kinase assay and in the in vivo human chronic myeloid leukemia K 562 cell growth inhibition assay described above, are set out in following Table 1.

TABLE 1

Inhibition of p45 v-abl kinase and K562 cell growth

| Compound | IC$_{50}$ (μM) | |
|---|---|---|
| | v-abl | K562 |
| FCE 27518 | 6.9 | 1.2 |
| FCE 27566 | 15.6 | 2.2 |
| FCE 27565 | 2.4 | — |
| FCE 27866 | 5.2 | 8.75 |
| FCE 27564 | 0.8 | 4.15 |
| FCE 27996 | 2.6 | 0.62 |
| FCE 28359 | 0.39 | 8.15 |
| FCE 28436 | 0.305 | 14.50 |
| FCE 28337 | 2.32 | 11.5 |
| FCE 28360 | 4.7 | 6.25 |

In the Table:
FCE 27518 means: 5-amino-3-[(8'-hydroxy-5'-quinolyl)methylene]-2-oxindole;
FCE 27566 means: 3-[(2'-methyl-3'-indolyl)methylene]-2-oxindole;
FCE 27565 means: 3-[(5'-cyano-3'-indolyl)methylene]-2-oxindole;
FCE 27866 means: 3-[(5'-hydroxy-3'-indolyl)methylene]-2-oxindole;
FCE 27564 means: 3-[(5'-methoxy-3'-indolyl)methylene]-2-oxindole;
FCE 27996 means: 5-bromo-3-[(8'-hydroxy-5'quinolyl)methylene]-2-oxindole;
FCE 28359 means: 5-hydroxy-3-[(5'-methoxy-3'-indolyl)methylene]-2-oxindole;
FCE 28436 means: 5-amino-3-[(5'-methoxy-3'-indolyl)methylene]-2-oxindole;
FCE 28337 means: 5-hydroxy-3-[(4'-hydroxy-1'-tetralyl)methylene]-2-oxindole;
FCE 28360 means: 5-amino-3-[(1',4'-dihydroxy-2'-tetralyl)methylene]-2-oxindole.

As can be appreciated from the activity data shown in Table 1, the compounds according to the invention are endowed with valuable biological properties.

In view of their high activity and low toxicity, the compounds of the invention can be used safely in medicine.

The compounds of the invention can be administered in a variety of dosage forms, e.g. orally, in the form of tablets, capsules, sugar or film-coated tablets, liquid solutions or suspensions; rectally, in the form of suppositories; parenterally, e.g. intramuscularly, or by intravenous injection or infusion; or topically.

The dosage depends on the age, weight, condition of the patient and administration route; for example, the dosage adopted for oral administration of the compounds 3-[(5'-methoxy-3'-indolyl)methylene]-2-oxindole and 5-bromo-3-[(8'-hydroxy-5'-quinolyl)methylene]-2-oxindole to adult humans may range from about 10 to about 150–200 mg per dose, from 1 to 5 times daily. Of course, these dosage regimens may be adjusted to provide the optimal therapeutic response.

The invention includes pharmaceutical compositions comprising a compound of the invention or a pharmaceutically acceptable salt thereof in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating or film-coating processes.

The liquid dispersion for oral administration may be e.g. syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusion may contain as carrier, for example, sterile water or, preferably, they may be in the form of sterile, aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin.

Compositions for topical application, e.g. creams, lotions, or pastes, can be prepared by mixing the active ingredient with a conventional oleaginous or emulsifying excipient.

Object of the present invention is also the use of a compound of formula (I)

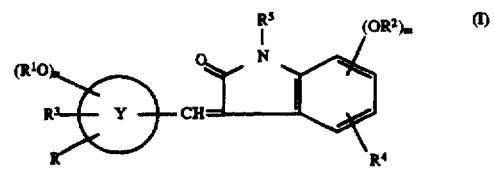

wherein

Y is a bicyclic ring system chosen from naphthalene, tetralin, quinoline and isoquinoline;

R is hydrogen or an oxo (=O) group when Y is tetralin, or R is hydrogen when Y is naphthalene, quinoline or isoquinoline;

each of R$^1$ and R$^2$ independently is hydrogen, C$_1$–C$_6$ alkyl or C$_2$–C$_6$ alkanoyl;

m is zero, 1 or 2;

n is zero, 1, 2 or 3;

each of R$^3$ and R$^4$ independently is hydrogen, halogen, cyano, C$_1$–C$_6$ alkyl, carboxy, nitro or —NR$^6$R$^7$ in which each of R$^6$ and R$^7$ independently is hydrogen or C$_1$–C$_6$ alkyl;

$R^5$ is hydrogen or $C_1$-$C_6$ alkyl; and the pharmaceutically acceptable salts thereof; and wherein a) when at the same time Y is naphthalene; $R^3$ is hydrogen, halogen, cyano or $C_1$-$C_6$ alkyl; $R^5$ is hydrogen; m is zero and n, R and $R^1$ are as defined above, then $R^4$ is other than hydrogen;

b) when at the same time Y is quinoline or isoquinoline; $R_3$ is hydrogen, halogen, cyano or $C_1$-$C_6$ alkyl; n is zero, 1 or 2; $R^5$ is hydrogen; m is zero and R and $R^1$ are as defined above, then $R^4$ is other than hydrogen; and c) when at the same time Y is tetralin in which only the benzene moiety is substituted, $R^3$ is hydrogen, halogen, cyano or $C_1$-$C_6$ alkyl; n is zero, 1 or 2; $R^5$ is hydrogen; m is zero, R is hydrogen and $R^1$ is as defined above, then $R^4$ is other than hydrogen;

in the preparation of a pharmaceutical composition for use as tyrosine kinase inhibitor, in particular in the treatment of the pathological disorders cited above.

A further object of the present invention is a combined method of treatment of cancer or of amelioration of the conditions of mammals, including humans, suffering from cancer, said method comprising administering 1) a compound of the invention, or a pharmaceutically acceptable salt thereof, and 2) an additional antitumor agent, in amounts and close enough together in time sufficient to produce a therapeutically useful effect.

The present invention also provides products containing a compound of the invention, or a pharmaceutically acceptable salt thereof, and an additional antitumour agent as a combined preparation for simultaneous, separate or sequential use in anti-cancer therapy.

The term "antitumor agent" is meant to comprise both a single antitumor drug and "cocktails" i.e. a mixture of such drugs, according to the clinical practice.

Examples of antitumor agents that can be formulated with a compound of the invention or alternatively, can be administered in a combined method of treatment, include doxorubicin, daunomycin, epirubicin, idarubicin, etoposide, fluoro-uracil, melphalan, cyclophosphamide, bleomycin, vinblastin and mitomycin or a mixtures of two or more thereof.

The compounds of the invention can therefore be used in a treatment to ameliorate a cancer. They may be administered to a patient suffering from a cancer treatable with an antitumor agent, for example an anthracycline glycoside such as doxorubicin, daunomycin, epirubicin or idarubicin as mentioned above, together with the antitumor agent.

A compound of the invention and an antitumor agent such as an anthracycline glycoside can be administered to improve the condition of a patient having a leukaemia such as myeloblastic leukaemia, lymphoma, sarcoma, neuroblastoma, Wilm's tumor or malignant neoplasm of the bladder, breast, lung or thyroid.

The following examples illustrate but do not limit the invention.

EXAMPLE 1

5-hydroxy-3-[(8'-hydroxy-5'-quinolyl)methylene]-2-oxindole

A solution of 8-hydroxyquinoline-5-carboxaldehyde (173 mg, 1 mmol), 5-hydroxy-2-oxindole (149 mg, 1 mmol) and piperidine (60 mg, 0.7 mmol) in absolute ethanol (10 ml) was heated for 3 h at 60°–70° C. under nitrogen. Then the reaction mixture was chilled and evaporated under vacuum to dryness. The residue was submitted to column chromatography over silica gel using dichloromethane/ethanol 4% as eluant to give pure title compound in about 60% yield.

Alternatively, the reaction mixture was concentrated under vacuum and then chilled to 0°–5° C., the precipitate filtered, the residue washed with ice-cooled ethanol and finally dried under vacuum. Compounds of higher purity are obtained by further crystallization from ethanol.

| $C_{18}H_{12}N_2O_3$ | requires: | C 71.05 | H 3.98 | N 9.20 |
|---|---|---|---|---|
| | found: | C 71.01 | H 3.85 | N 9.15 |

MS m/z 304

NMR δ ppm: 6.5–6.7 (m,3H), 7.20 (d,1H), 7.62 (dd,1H), 7.83 (d,1H), 7.93 (s,1H), 8.33 (dd,1H), 8.85 (bs,1H), 8.93 (dd,1H), 10.30 (bs,1H).

According to the above described procedure, the following compounds can be prepared:

5-amino-3-[(8'-hydroxy-5'-quinolyl)methylene]-2-oxindole;

| $C_{18}H_{13}N_3O_2$ | requires: | C 74.98 | H 4.20 | N 9.72 |
|---|---|---|---|---|
| | found: | C 74.76 | H 4.31 | N 9.43 |

MS m/z 288

NMR δ ppm: 6.4–6.6 (mm,3H), 7.18 (d,1H), 7.62 (dd, 1H), 7.84 (d,1H), 7.87 (s,1H), 8.34 (dd,1H), 8.93 (dd,1H), 10.14 (bs,1H).

3-[(2'-methyl-3'-indolyl)methylene]-2-oxindole

| $C_{18}H_{14}N_2O$ | requires: | C 78.81 | H 5.14 | N 10.21 |
|---|---|---|---|---|
| | found: | C 78.56 | H 5.01 | N 10.11 |

MS m/z 274

NMR δ ppm: 2.46 (s,3H), 6.7–6.8 (m,2H), 6.85 (d,1H), 7.0–7.2 (m,4H), 7.41 (d,1H), 7.80 (s,1H), 10.48 (bs,1H), 11.86 (bs,1H).

3-[(5'-cyano-3'-indolyl)methylene]-2-oxindole

| $C_{18}H_{11}N_3O$ | requires: | C 75.77 | H 3.89 | N 14.73 |
|---|---|---|---|---|
| | found: | C 75.71 | H 3.55 | N 14.51 |

MS m/z 285

NMR δ ppm: 6.8–7.2 (m,3H), 7.57 (dd,1H), 7.69 (d,1H), 7.95 (d,1H), 8.21 (s,1H), 8.85 (d,1H), 9.52 (s,1H), 10.62 (bs,1H), 12.4 (bs,1H).

3-[(5'-hydroxy-3'-indolyl)methylene]-2-oxindole

| $C_{17}H_{12}N_2O_2$ | requires: | C 73.89 | H 4.38 | N 10.14 |
|---|---|---|---|---|
| | found: | C 73.55 | H 4.36 | N 9.97 |

MS m/z 276

NMR δ ppm: 6.75 (m,1H), 6.82 (d,1H), 6.9–7.0 (m,1H), 7.0–7.2 (m,1H), 7.29 (d,1H), 7.42 (d,1H), 7.80 (d,1H), 7.97 (s,1H), 8.96 (s,1H), 9.34 (d,1H), 10.42 (s,1H), 11.8 (bs,1H).

3-[(5'-methoxy-3'-indolyl)methylene]-2-oxindole

| $C_{18}H_{14}N_2O_2$ | requires: | C 74.47 | H 4.86 | N 9.65 |
|---|---|---|---|---|
| | found: | C 74.35 | H 4.72 | N 9.54 |

MS m/z 290
NMR δ ppm: 3.87 (s,3H), 6.8–6.9 (m,2H), 7.12 (ddd,1H), 7.38 (d,1H), 7.72 (d,1H), 7.91 (d,1H), 8.13 (s,1H), 9.40 (s,1H), 10.49 (bs,1H), 11.88 (bs,1H).

3-[(8'-hydroxy-7'-quinolyl)methylene]-2-oxindole

| $C_{18}H_{12}N_2O_2$ | requires: | C 74.98 | H 4.20 | N 9.72 |
|---|---|---|---|---|
| | found: | C 79.81 | H 4.31 | N 9.43 |

MS m/z 288
NMR δ ppm: 6.8–6.9 (m,2H), 7.21 (t,1H), 7.48 (m,2H), 7.64 (dd,1H), 7.81 (d,1H), 7.89 (s,1H), 8.38 (dd,1H), 8.91 (dd,1H), 10.6 (bs,1H).

5-hydroxy-3-[(2'-methyl-3'-indolyl)methylene]-2-oxindole
NMR δ ppm: 2.42 (s,3H), 6.30 (d,1H), 6.54 (dd,1H), 6.63 (d,1H), 7.0–7.2 (m,3H), 7.41 (d,1H), 7.73 (s,1H), 8.71 (s,1H), 10.16 (s,1H), 11.79 (s,1H).

3-[(4'-amino-1'-tetralyl)methylene]-2-oxindole;
3-[(4'-dimethylamino-1'-tetralyl)methylene]-2-oxindole;
3-[(4'-carboxy-1'-tetralyl)methylene]-2-oxindole;
5-hydroxy-3-[(1'-tetralyl)methylene]-2-oxindole;
5-amino-3-[(1'-tetralyl)methylene]-2-oxindole;
5-carboxy-3-[(1'-tetralyl)methylene]-2-oxindole;
5-hydroxy-3-[(2'-hydroxy-1'-tetralyl)methylene]-2-oxindole;
5-hydroxy-3-[(4'-hydroxy-1'-tetralyl)methylene]-2-oxindole NMR δ ppm: 1.69 (m,4H), 2.5–2.7 (m,4H), 6.57 (dd,1H), 6.62 (d,1H), 6.72 (d,1H), 6.88 (d,1H), 7.26 (d,1H), 7.53 (s,1H), 8.87 (s,1H), 9.8 (bs,1H), 10.17 (s,1H).

5-amino-3-[(2'-hydroxy-1'-tetralyl)methylene]-2-oxindole;
5-amino-3-[(4'-hydroxy-1'-tetralyl)methylene]-2-oxindole;
5-carboxy-3-[(2'-hydroxy-1'-tetralyl)methylene]-2-oxindole;
5-carboxy-3-[(4'-hydroxy-1'-tetralyl)methylene]-2-oxindole;
5-hydroxy-3-[(4',5'-dihydroxy-1'-tetralyl)methylene]-2-oxindole;
5-hydroxy-3-[(4',8'-dihydroxy-1'-tetralyl)methylene]-2-oxindole;
5-amino-3-[(4',5'-dihydroxy-1'-tetralyl)methylene]-2-oxindole;
5-amino-3-[(4',8'-dihydroxy-1'-tetralyl)methylene]-2-oxindole;
5-carboxy-3-[(4',5'-dihydroxy-1'-tetralyl)methylene]-2-oxindole;
3-[(4'-amino-2'-tetralyl)methylene]-2-oxindole;
3-[(4'-carboxy-2'-tetralyl)methylene]-2-oxindole;
5-hydroxy-3-[(2'-tetralyl)methylene]-2-oxindole;
5-amino-3-[(2'-tetralyl)methylene]-2-oxindole;
5-carboxy-3-[(2'-tetralyl)methylene]-2-oxindole;
5-hydroxy-3-[(1'-hydroxy-2'-tetralyl)methylene]-2-oxindole;
5-hydroxy-3-[(3'-hydroxy-2'-tetralyl)methylene]-2-oxindole;
5-hydroxy-3-[(4'-hydroxy-2'-tetralyl)methylene]-2-oxindole;
5-amino-3-[(1'-hydroxy-2'-tetralyl)methylene]-2-oxindole;
5-amino-3-[(3'-hydroxy-2'-tetralyl)methylene]-2-oxindole;
5-amino-3-[(4'-hydroxy-2'-tetralyl)methylene]-2-oxindole;
5-carboxy-3-[(1'-hydroxy-2'-tetralyl)methylene]-2-oxindole;
5-carboxy-3-[(3'-hydroxy-2'-tetralyl)methylene]-2-oxindole;
5-carboxy-3-[(4'-hydroxy-2'-tetralyl)methylene]-2-oxindole;
5-hydroxy-3-[(1',4'-dihydroxy-2'-tetralyl)methylene]-2-oxindole;
5-hydroxy-3-[(4',5'-dihydroxy-2'-tetralyl)methylene]-2-oxindole;
5-hydroxy-3-[(4',8'-dihydroxy-2'-tetralyl)methylene]-2-oxindole;
5-hydroxy-3-[(3',5'-dihydroxy-2'-tetralyl)methylene]-2-oxindole;
5-hydroxy-3-[(3',8'-dihydroxy-2'-tetralyl)methylene]-2-oxindole;
5-amino-3-[(1',4'-dihydroxy-2'-tetralyl)methylene]-2-oxindole NMR δ ppm: 1.69 (m,4H), 2.58 (m,4H), 6.86 (s,1H), 6.94 (d,1H), 7.15 (dd,1H), 7.60 (d,1H), 7.75 (s,1H), 8.4 (bs,1H), 8.9 (bs,1H), 9.7 (bs,3H), 10.71 (s,1H).

5-amino-3-[(4',5'-dihydroxy-2'-tetralyl)methylene]-2-oxindole;
5-amino-3-[(4',8'-dihydroxy-2'-tetralyl)methylene]-2-oxindole;
5-amino-3-[(3',5'-dihydroxy-2'-tetralyl)methylene]-2-oxindole;
5-amino-3-[(3',8'-dihydroxy-2'-tetralyl)methylene]-2-oxindole;
5-carboxy-3-[(1',4'-dihydroxy-2'-tetralyl)methylene]-2-oxindole;
5-carboxy-3-[(4',5'-dihydroxy-2'-tetralyl)methylene]-2-oxindole;
5-carboxy-3-[(4',8'-dihydroxy-2'-tetralyl)methylene]-2-oxindole;
5-carboxy-3-[(3',5'-dihydroxy-2'-tetralyl)methylene]-2-oxindole;
5-carboxy-3-[(3',8'-dihydroxy-2'-tetralyl)methylene]-2-oxindole;
5-hydroxy-3-[(1',4',5'-trihydroxy-2'-tetralyl)methylene]-2-oxindole;
5-hydroxy-3-[(1',4',8'-trihydroxy-2'-tetralyl)methylene]-2-oxindole;
3-[(8'-oxo-1',4'-dihydroxy-2'-tetralyl)methylene]-2-oxindole NMR δ ppm: 2.03 (m,2H), 2.70 and 2.89 (two m,4H), 6.7–7.0 (m,2H), 7.1–7.3 (m,1H), 7.51 (s,1H), 7.54 (d,1H), 7.58 (d,1H), 7.61 (s,1H), 7.87 (s,1H), 8.46 (s,1H), 9.38 (s,1H), 9.56 (s,1H), 10.58 (s,1H), 10.59 (s,1H), 12.5 (bs,1H), 12.8 (bs,1H).

5-hydroxy-3-[(5'-quinolyl)methylene]-2-oxindole;
5-amino-3-[(5'-quinolyl)methylene]-2-oxindole;
5-carboxy-3-[(5'-quinolyl)methylene]-2-oxindole;
5-hydroxy-3-[(4'-quinolyl)methylene]-2-oxindole;

5-amino-3-[(4'-quinolyl)methylene]-2-oxindole;

5-carboxy-3-[(4'-quinolyl)methylene]-2-oxindole;

5-carboxy-3-[(8'-hydroxy-5'-quinolyl)methylene]-2-oxindole;

5-hydroxy-3-[(8'-hydroxy-4'-quinolyl)methylene]-2-oxindole;

5-amino-3-[(8'-hydroxy-4'-quinolyl)methylene]-2-oxindole;

5-carboxy-3-[(8'-hydroxy-4'-quinolyl)methylene]-2-oxindole;

5-bromo-3-[(8'-hydroxy-5'-quinolyl)methylene]-2-oxindole

NMR δ ppm: 6.76 (d,1H), 6.83 (d,1H), 7.12 (d,1H), 7.17 (d,1H), 7.22 (d,1H), 7.3–7.4 (m,2H), 7.6–7.7 (m,2H), 7.89 (d,1H), 8.08 (s,1H), 8.17 (d,1H), 8.36 (dd,1H), 8.46 (s,1H), 8.8–9.0 (m,4H), 10.66 (s,1H), 10.77 (s,1H).

5-fluoro-3-[(8'-hydroxy-5'-quinolyl)methylene]-2-oxindole

NMR δ ppm: 6.8–6.9 (m,2H), 7.04 (ddd,1H), 7.22 (d,1H), 7.63 (dd,1H), 7.89 (d,1H), 8.08 (s,1H), 8.37 (dd,1H), 8.94 (dd,1H), 10.5 (bs,1H), 10.65 (s,1H).

3-[(5'-hydroxy-4'-quinolyl)methylene]-2-oxindole;

3-[(8'-hydroxy-4'-quinolyl)methylene]-2-oxindole;

5hydroxy-3-[(5'-methoxy-3'-indolyl)methylene]-2-oxindole

NMR δ ppm: 3.86 (s,3H), 6.5–6.7 (m,2H), 6.82 (dd,1H), 7.36 (m,2H), 7.68 (d,1H), 7.99 (s,1H), 8.82 (s,1H), 9.37 (d,1H), 10.15 (s,1H), 11.8 (bs,1H).

5-amino-3-[(5'-methoxy-3'-indolyl)methylene]-2-oxindole

NMR δ ppm: 3.87 (s,3H), 6.87 (dd,1H), 6.90 (d,1H), 7.07 (dd,1H), 7.42 (d,1H), 7.66 (d,1H), 7.81 (d,1H), 8.18 (s,1H), 9.44 (d,1H), 9.65 (bs,3H), 10.67 (s,1H), 12.03 (d,1H), and 5-hydroxy-3-[(2'-methyl-3'-indolyl)methylene]-2-oxindole

EXAMPLE 2

5-hydroxy-3-[(1'-tetralyl)methylene]-2-oxindole

To a stirred solution of 5-methoxy-3-[(1'-tetralyl)methylene]-2-oxindole (305 mg, 1 mmol) in anhydrous dichloromethane (10 ml) was added at −78° C. under nitrogen, over a period of 10 min, a 1.0M solution of boron tribromide in dichloromethane (3 ml, 3 mmol). The resulting mixture was stirred for another 1 h at −78° C. and then allowed to warm up to room temperature. After stirring for 1.5 h at 20°–25° C. the mixture was cooled to −10° C. and then quenched by dropwise addition of water (10 ml) over a 10-min period. After addition of ethyl acetate the organic layer was separated, washed with water, dried with $Na_2SO_4$ and evaporated under vacuum to dryness. The residue was crystallized from ethanol thus giving pure title compound in 70% yield.

| $C_{19}H_{17}NO_2$ | requires: | C 78.30 | H 5.88 | N 4.81 |
|---|---|---|---|---|
| | found: | C 78.15 | H 5.75 | N 4.71 |

MS m/z 291

IR cm$^{-1}$: 3600-2600 (NH,OH), 1655 (amide), 1610 (amide), 1585, 1535 (C=C).

EXAMPLE 3

5-amino-3-[(1'-tetralyl)methylene]-2-oxindole

To a solution of 5-nitro-3-[(1'-tetralyl)methylene]-2-oxindole (320 mg, 1 mmol) in anhydrous ethanol (20 ml) was added palladium on charcoal (20 mg) and the mixture was hydrogenated at room temperature and atmospheric pressure until 3 equivalent of hydrogen has been taken up. The hydrogen uptake was graphed as a function of time. The catalyst was filtered and the solution concentrated under vacuum until crystallization began. Then the mixture was cooled to 0°–5° C., filtered, the residue washed with ice-cooled ethanol and dried under vacuum. Thus almost pure title compound was obtained in about 80% yield.

| $C_{19}H_{18}N_2O$ | requires: | C 78.59 | H 6.25 | N 9.65 |
|---|---|---|---|---|
| | found: | C 78.45 | H 6.13 | N 9.55 |

MS m/z 290

IR cm$^{-1}$: 3400-3200 (NH), 1660 (amide), 1610 (amide) 1580, 1530 (C=C).

EXAMPLE 4

5-methoxy-3-[(2'-tetralyl)methylene]-2-oxindole

To a suspension of 95% sodium hydride (28 mg, 1.1 mmol) in DMF (10 ml) cooled with an ice-propanol bath was added over 15 min with stirring a solution of 5-hydroxy-3-[(2'-tetralyl)methylene]-2-oxindole (291 mg, 1 mmol) in DMF (5 ml). When the evolution of hydrogen stopped, a solution of iodomethane (156 mg, 1.1 mmol) in DMF (5 ml) was added over 15 min and the mixture was stirred at room temperature for 3 h. Most of the DMF was distilled off in vacuum, water was then added to the residue and the product extracted into ethylacetate. The organic solution containing the desired product was dried, the solvent evaporated and the remaining oil was crystallized by trituration with ethanol. Thus pure title compound was obtained in about 60% yield.

| $C_{20}H_{19}NO_2$ | requires: | C 78.66 | H 6.27 | N 4.59 |
|---|---|---|---|---|
| | found: | C 78.51 | H 6.11 | N 4.35 |

MS m/z 305

IR cm$^{-1}$: 3400-3200, 1655, 1605 (amide), 1580, 1530 (C=C).

EXAMPLE 5

5-acetoxy-3-[(2'-tetralyl)methylene]-2-oxindole

To a cooled solution of 5-hydroxy-3-[(2'-tetralyl)methylene]-2-oxindole (291 mg, 1 mmol) in dry pyridine (0.5 ml) was added acetic anhydride (306 mg, 3 mmol) and the mixture maintained at 0°–5° C. overnight. Thereupon the mixture was concentrated under vacuum, the residue dissolved in dichloromethane, the organic layer washed with water and then evaporated under reduced pressure. The crude product was crystallized from chloroform/methanol to yield almost pure title compound in about 80% yield.

| $C_{21}H_{19}NO_3$ | requires: | C 75.66 | H 5.74 | N 4.20 |
|---|---|---|---|---|
| | found: | C 75.59 | H 5.81 | N 4.15 |

MS m/z 333.

EXAMPLE 6

1,4-dihydroxy-2-tetralincarboxaldehyde

To a solution of 1,4-dihydroxy-tetralin (1.640 g, 0.010 mol) in dichloromethane (50 ml) was added titanium tetrachloride (5.69 g, 0.03 mol). Then 1,1-dichlorodimethyl ether (1.73 g, 0.015 mol) was added dropwise under vigorous stirring and the reaction mixture stirred for another 3 h at room temperature. Finally 5% hydrochloric acid (10 ml) was added under ice-cooling. The organic phase was separated and the residual aqueous phase repeatedly extracted with ether. The combined organic phases are washed with saturated saline solution, dried over sodium sulfate and evaporated under vacuum. The residue was crystallized from benzene or alternatively submitted to flash chromatography on silica gel with benzene/ethylacetate 85:15 to afford pure title compound in about 60% yield (1.080 g), m.p. 145° C.

MS m/z 180

NMR δ ppm: 10.4 (bs, OH), 9.7 (s, CHO), 9.1 (bs, OH), 6.9 (s, H arom), 2.8 (m, 5-$CH_2$, 8-$CH_2$), 1.9 (m, 6-$CH_2$, 7-$CH_2$).

EXAMPLE 7

By proceeding according to the technique of above Example 1 and Examples 1, 2 and 7 of WO 91/13055 and starting from a suitable quinoline-, tetralin- or naphthalene-carboxaldehyde and cyanoacetamide, cyanothioacetamide or 4-hydroxybenzylcyanide the following compounds can be obtained.

2-(4-hydroxyphenyl)-3-(1,4-dimethoxy-2-naphthyl)acrylonitrile

| $C_{16}H_{14}N_2O_3$ | requires: | C 68.07 | H 5.00 | N 9.93 |
|---|---|---|---|---|
| | found: | C 67.98 | H 5.02 | N 9.92 |

MS m/z 282
NMR δ ppm: 3.90 (3H,s), 3.99 (3H,s), 7.60 (1H,s), 7.70 (2H,m), 7.8, 8.0 (2H, two S), 8.15 (2H,m), 8.49 (1H,s).

2-cyano-3-(4-quinolyl)acrylamide

| $C_{13}H_9N_3O$ | requires: | C 69.95 | H 4.06 | N 18.82 |
|---|---|---|---|---|
| | found: | C 69.86 | H 4.01 | N 18.75 |

MS m/z 223
IR $cm^{-1}$: 3400, 3299 (NH), 2210 (CN), 1680 (CO), 1610, 1590, 1580 (C=C).

2-cyano-3-(3-indolyl)acrylamide

| $C_{12}H_9N_3O$ | requires: | C 68.24 | H 4.29 | N 19.89 |
|---|---|---|---|---|
| | found: | C 68.11 | H 4.21 | N 19.85 |

MS m/z 211
IR $cm^{-1}$: 3400, 3150 (NH), 2220 (CN), 1680 (CO), 1605, 1590, 1580 (C=C).

2-cyano-3-(1,4-dihydroxy-2-tetralyl)acrylamide

| $C_{14}H_{14}N_2O_3$ | requires: | C 65.10 | H 5.46 | N 10.85 |
|---|---|---|---|---|
| | found: | C 65.16 | H 5.58 | N 10.67 |

MS m/z 258
IR $cm^{-1}$: 3200–3400 (NH,OH), 2210 (CN), 1680 (CO), 1610, 1595 (C=C).

2-cyano-3-(1,4-dihydroxy-2-tetralyl)thioacrylamide

| $C_{14}H_{14}N_2O_2S$ | requires: | C 61.30 | H 5.14 | N 10.21 | S 11.69 |
|---|---|---|---|---|---|
| | found: | C 61.25 | H 5.01 | N 10.05 | S 11.65 |

MS m/z 274
IR $cm^{-1}$: 3100–3400 (NH,OH), 2200 (CN), 1620, 1570 (C=C).

2-cyano-3-(2-hydroxy-1-naphthyl)acrylonitrile

| $C_{14}H_8N_2O$ | requires: | C 76.33 | H 3.66 | N 12.72 |
|---|---|---|---|---|
| | found: | C 76.11 | H 3.71 | N 12.73 |

MS m/z 220
NMR δ ppm: 7.36 (d,1H), 7.5–7.9 (m,2H), 7.99 (d,1H), 8.17 (d,1H), 9.47 (d,1H), 8.79 (d,1H), 9.17 (d,1H).

2-cyano-3-(2-naphthyl)acrylamide

| $C_{14}H_{10}N_2O$ | requires: | C 75.66 | H 4.54 | N 12.60 |
|---|---|---|---|---|
| | found: | C 75.63 | H 4.51 | N 12.65 |

MS m/z 225
IR $cm^{-1}$: 3390 (NH), 3180 (NH), 2210 (CN), 1690 (CO), 1615 (amide), 1595, 1585 (arom).

2-cyano-3-(2-naphthyl)thioacrylamide

| $C_{14}H_{10}N_2S$ | requires: | C 70.56 | H 4.23 | N 11.76 | S 13.45 |
|---|---|---|---|---|---|
| | found: | C 69.12 | H 4.35 | N 11.98 | S 13.10 |

MS m/z 238
NMR δ ppm: 7.65 (2H,m), 8.05 (4H,m), 8.24 (1H,s), 8.44 (1H,s), 9.68, 10.15 (2H,bs).

2-cyano-3-(3,5-dihydroxy-2-naphthyl)acrylamide

| $C_{14}H_{10}N_2O_3$ | requires: | C 66.13 | H 3.97 | N 11.02 |
|---|---|---|---|---|
| | found: | C 66.98 | H 3.85 | N 10.72 |

MS m/z 254.

EXAMPLE 8

Tablets each weighing 0.150 g and containing 25 mg of the active substance, can be manufactured as follows: composition (for 10,000 tablets):

| | |
|---|---|
| 5-amino-3-[(8'-hydroxy-5'-quinolyl)methylene]-2-oxindole | 250 g |
| Lactose | 800 g |
| Corn starch | 415 g |
| Talc powder | 30 g |
| Magnesium stearate | 5 g |

The 5-amino-3-[(8'-hydroxy-5'-quinolyl)methylene]-2-oxindole, the lactose and half the corn starch are mixed; the mixture is then forced through a sieve of 0.5 mm mesh size.

Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

EXAMPLE 9

Capsules, each dosed at 0.200 g and containing 20 mg of the active substance can be prepared: composition for 500 capsules:

| | |
|---|---|
| 3-[(5'-methoxy-3'-indolyl)methylene]-2 oxindole | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

We claim:

1. A compound having the following general formula (I)

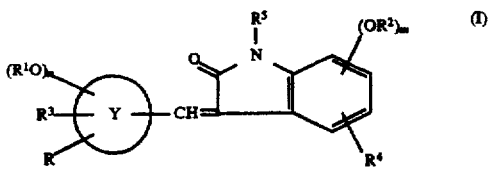

wherein

Y is a moiety selected from the group consisting of naphthyl, tetrayl, quinolyl and isoquinolyl;

R is hydrogen or an oxo (=O) group when Y is tetralin; or R is hydrogen when Y is naphthyl, quinolyl or isoquinolyl;

each of $R^1$ and $R^2$ independently is hydrogen, $C_1-C_6$ alkyl or $C_2-C_6$ alkanoyl;

m is zero, 1 or 2;

n is zero, 1, 2 or 3;

each of $R^1$ and $R^4$ independently is hydrogen, halogen, cyano, $C_1-C_6$ alkyl, carbon, nitro or $-NR^6R^7$ in which each of $R^6$ and $R^7$ independently is hydrogen or $C_1-C_6$ alkyl;

$R^5$ is hydrogen or $C_1-C_6$ alkyl; or a pharmaceutically acceptable salt thereof; with the provisos that a) when at the same time Y is naphthyl; $R^3$ is hydrogen, halogen, cyano or $C_1-C_6$ alkyl; $R^5$ is hydrogen; m is zero and n, R and $R^1$ are as defined above, then $R^4$ is other than hydrogen;

b) when at the same time Y is quinolyl or isoquinolyl; $R_3$ is hydrogen, halogen, cyano or $C_1-C_6$ alkyl; n is zero, 1 or 2; $R^5$ is hydrogen; m is zero and R and $R^1$ are as defined above, then $R^4$ is other than hydrogen;

c) when at the same time Y is tetralyl in which only the benzene moiety is substituted, $R^3$ is hydrogen, halogen, cyano or $C_1-C_6$ alkyl; n is zero, 1 or 2; $R^5$ is hydrogen; m is zero, R is hydrogen and $R^1$ is as defined above, then $R^4$ is other than hydrogen;

and d) when at the same time Y is naphthyl; m and n are zero; R and $R^3$ are hydrogen; $R^4$ being linked at the C-4 carbon atom is halogen or $C_1-C_4$ alkyl, then $R^5$ is other than $C_1-C_2$ alkyl.

2. The compound of claim 1, wherein

Y is tetralyl, quinolyl or isoquinolyl;

n is zero, 1, 2 or 3;

m is zero or 1;

each of $R^1$ and $R^2$ independently is hydrogen or $C_1-C_4$ alkyl;

each of $R^3$ and $R^4$ independently is hydrogen, halogen, cyano, carboxy or amino;

$R^5$ is hydrogen; and

R is defined in claim 1; or a pharmaceutically acceptable salt thereof.

3. The compound of claim 1, wherein,

Y is tetralyl or quinolyl;

n is zero, 1, 2 or 3;

m is zero or 1;

$R^1$, $R^2$ and $R^5$ are hydrogen;

each of $R^3$ and $R^4$ independently is hydrogen, amino or carboxy; and

R is as defined in claim 1, or a pharmaceutically acceptable salt thereof.

4. A compound selected from

3-[(4'-amino-1'-tetralyl)methylene]-2-oxindole;
3-[(4'-dimethylamino-1'-tetralyl)methylene]-2-oxindole;
3-[(4'-carboxy-1'-tetralyl)methylene]-2-oxindole;
5-hydroxy-3-[(1'-tetralyl)methylene]-2-oxindole;
5-amino-3-[(1'-tetralyl)methylene]-2-oxindole;
5-carboxy-3-[(1'-tetralyl)methylene]-2-oxindole;
5-hydroxy-3-[(2'-hydroxy-1'-tetralyl)methylene]-2-oxindole;
5-hydroxy-3-[(4'-hydroxy-1'-tetralyl)methylene]-2-oxindole;
5-amino-3-[(2'-hydroxy-1'-tetralyl)methylene]-2-oxindole;
5-amino-3-[(4'-hydroxy-1'-tetralyl)methylene]-2-oxindole;
5-carboxy-3-[(2'-hydroxy-1'-tetralyl)methylene]-2-oxindole;
5-carboxy-3-[(4'-hydroxy-1'-tetralyl)methylene]-2-oxindole;
5-hydroxy-3-[(4',5'-dihydroxy-1'-tetralyl)methylene]-2-oxindole;
5-hydroxy-3-[(4',8'-dihydroxy-1'-tetralyl)methylene]-2-oxindole;
5-amino-3-[(4',5'-dihydroxy-1'-tetralyl)methylene]-2-oxindole;
5-amino-3-[(4',5'-dihydroxy-1'-tetralyl)methylene]-2-oxindole;
5-carboxy-3-[(4',5'-dihydroxy-1'-tetralyl)methylene]-2-oxindole;
3-[(4'-amino-2'-tetralyl)methylene]-2-oxindole;
3-[(4'-carboxy-2'-tetralyl)methylene]-2-oxindole;
5-hydroxy-3-[(2'-tetralyl)methylene]-2-oxindole;
5-amino-3-[(2'-tetralyl)methylene]-2-oxindole;
5-carboxy-3-[(2'-tetralyl)methylene]-2-oxindole;
5-hydroxy-3-[(1'-hydroxy-2'-tetralyl)methylene]-2-oxindole;
5-hydroxy-3-[(3'-hydroxy-2'-tetralyl)methylene]-2-oxindole;
5-hydroxy-3-[(4'-hydroxy-2'-tetralyl)methylene]-2-oxindole;
5-amino-3-[(1'-hydroxy-2'-tetralyl)methylene]-2-oxindole
5-amino-3-[(3'-hydroxy-2'-tetralyl)methylene]-2-oxindole;
5-amino-3-[(4'-hydroxy-2'-tetralyl)methylene]-2-oxindole;

5-carboxy-3-[(1'-hydroxy-2'-tetralyl)methylene]-2-oxindole;

5-carboxy-3-[(3'-hydroxy-2'-tetralyl)methylene]-2-oxindole;

5-carboxy-3-[(4'-hydroxy-2'-tetralyl)methylene]-2-oxindole;

5-hydroxy-3-[(1',4'-dihydroxy-2'-tetralyl)methylene]-2-oxindole;

5-hydroxy-3-[(4',5'-dihydroxy-2'-tetralyl)methylene]-2-oxindole;

5-hydroxy-3-[(4',8'-dihydroxy-2'-tetralyl)methylene]-2-oxindole;

5-hydroxy-3-[(3',5'-dihydroxy-2'-tetralyl)methylene]-2-oxindole;

5-hydroxy-3-[(3',8'-dihydroxy-2'-tetralyl)methylene]-2oxindole;

5-amino-3-[(1',4'-dihydroxy-2'-tetralyl)methylene]-2-oxindole;

5-amino-3-[(4',5'-dihydroxy-2'-tetralyl)methylene]-2-oxindole;

5-amino-3-[(4',8'-dihydroxy-2'-tetralyl)methylene]-2-oxindole;

5-amino-3-[(3',5'-dihydroxy-2'-tetralyl)methylene]-2-oxindole;

5-amino-3-[(3',8'-dihydroxy-2'-tetralyl)methylene]-2-oxindole;

5-carboxy-3-[(1',4'-dihydroxy-2'-tetralyl)methylene]-2-oxindole;

5-carboxy-3-[(4',5'-dihydroxy-2'-tetralyl)methylene]-2-oxindole;

5-carboxy-3-[(4',8'-dihydroxy-2'-tetralyl)methylene]-2-oxindole;

5-carboxy-3-[(3',5'-dihydroxy-2'-tetralyl)methylene]-2-oxindole;

5-carboxy-3-[(3',8'-dihydroxy-2'-tetralyl)methylene]-2-oxindole;

5-hydroxy-3-[(1',4',5'-trihydroxy-2'-tetralyl)methylene]-2-oxindole;

5-hydroxy-3-[(1',4',8'-trihydroxy-2'-tetralyl)methylene]-2-oxindole;

3-[(8'-oxo-1',4'-dihydroxy-2'-tetralyl)methylene]-2-oxindole;

5-hydroxy-3-[(5'-quinolyl)methylene]-2-oxindole;

5-amino-3-[(5'-quinolyl)methylene]-2-oxindole;

5-carboxy-3-[(5'-quinolyl)methylene]-2-oxindole;

5-hydroxy-3-[(4'-quinolyl)methylene]-2-oxindole;

5-amino-3-[(4'-quinolyl)methylene]-2-oxindole;

5-carboxy-3-[(4'-quinolyl)methylene]-2-oxindole;

5-hydroxy-3-[(8'-hydroxy-5'-quinolyl)methylene]-2-oxindole;

5-amino-3-[(8'-hydroxy-5'-quinolyl)methylene]-2-oxindole;

5-carboxy-3-[(8'-hydroxy-5'-quinolyl)methylene]-2-oxindole;

5-hydroxy-3-[(8'-hydroxy-4'-quinolyl)methylene]-2-oxindole;

5-amino-3-[(8'-hydroxy-4'-quinolyl)methylene]-2-oxindole;

5-carboxy-3-[(8'-hydroxy-4'-quinolyl)methylene]-2-oxindole;

5-bromo-3-[(8'-hydroxy-5'-quinolyl)methylene]-2-oxindole;

5-fluoro-3-[(8'-hydroxy-5'-quinolyl)methylene]-2-oxindole;

5-methoxy-3-[(2'-tetralyl)methylene]-2-oxindole;

5-acethoxy-3-[(2'-tetralyl)methylene]-2-oxindole;

5-hydroxy-3-[(4'-hydroxy-1'-tetralyl)methylene]-2-oxindole;

pharmaceutically acceptable salt thereof.

5. A compound selected from:

3-[(8'-hydroxy-7'-quinolyl)methylene]-2-oxindole;

3-[(5'-hydroxy-4'-quinolyl)methylene]-2-oxindole;

3-[(8'-hydroxy-4'-quinolyl)methylene]-2-oxindole;

5-hydroxy-3-[(5'-methoxy-3'-indolyl)methylene]-2-oxindole;

5-amino-3-[(5'-methoxy-3'-indolyl)methylene]-2-oxindole;

5-hydroxy-3-[(2'-methyl-3'-indolyl)methylene]-2-oxindole;

3-[(2'-methyl-3'-indolyl)methylene]-2-oxindole;

3-[(5'-cyano-3'-indolyl)methylene]-2-oxindole;

3-[(5'-hydroxy-3'-indolyl)methylene]-2-oxindole; and

3-[(5'-methoxy-3'-indolyl)methylene]-2-oxindole.

or a pharmaceutically acceptable salt thereof.

6. The compound of claim 1, wherein Y is quinolyl.

7. The compound of claim 2, wherein Y is quinolyl.

8. The compound of claim 3, wherein Y is quinolyl.

9. A compound selected from the group consisting of 5-hydroxy-3-[(5'-quinolyl)methylene]-2-oxindole;

5-amino-3-[(5'-quinolyl)methylene]-2-oxindole;

5-carboxy-3-[(5'-quinolyl)methylene]-2-oxindole;

5-hydroxy-3-[(4'-quinolyl)methylene]-2-oxindole;

5-amino-3-[(4'-quinolyl)methylene]-2-oxindole;

5-carboxy-3-[(4'-quinolyl)methylene]-2-oxindole;

5-hydroxy-3-[(8'-hydroxy-5'-quinolyl)methylene]-2-oxindole;

5-amino-3-[(8'-hydroxy-5'-quinolyl)methylene]-2-oxindole;

5-carboxy-3-[(8'-hydroxy-5'-quinolyl)methylene]-2-oxindole;

5-hydroxy-3-[(8'-hydroxy-4'-quinolyl)methylene]-2-oxindole;

5-amino-3-[(8'-hydroxy-4'-quinolyl)methylene]-2-oxindole;

5-carboxy-3-[(8'-hydroxy-4'-quinolyl)methylene]-2-oxindole;

5-bromo-3-[(8'-hydroxy-5'-quinolyl)methylene]-2-oxindole; and 5-fluoro-3-[(8'-hydroxy-5'-quinolyl)methylene]-2-oxindole;

or a pharmaceutically acceptable salt thereof.

10. A compound selected from the group consisting of:

3-[(8'-hydroxy-7'-quinolyl)methylene]-2-oxindole;

3-[(5'-hydroxy-4'-quinolyl)methylene]-2-oxindole; and

3-[(8'-hydroxy-4'-quinolyl)methylene]-2-oxindole;

or a pharmaceutically acceptable salt thereof.

11. The compound according to claim 1, which is 5-bromo-3-[(8'-hydroxy-5'-quinolyl)methylene]-2-oxindole.

12. A pharmaceutical composition containing a suitable carrier and/or diluent and, as an active principle, a compound of formula (I) according to claim 1 or a pharmaceutically acceptable salt thereof.

13. A method of inhibiting tyrosine kinase in a patient in need thereof, the method comprising administering to said patient a therapeutically effective amount of a compound of formula (I)

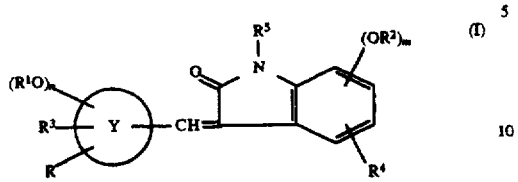

wherein
Y is a a moiety selected from the group consisting of naphthyl, tetrayl, quinolyl and isoquinolyl;
R is hydrogen or an oxo (=O) group when Y is tetralyl, or R is hydrogen when Y is naphthyl, quinolyl or isoquinolyl;
each of $R^1$ and $R^2$ independently is hydrogen $C_1$-$C_6$ alkyl or $C_2$-$C_6$ alkanoyl;
m is zero, 1 or 2;
n is zero, 1, 2 or 3;
each of $R^3$ and $R^4$ independently is hydrogen, halogen, cyano, $C_1$-$C_6$ alkyl, carboxy, nitro or —$NR^6R^7$ in which each of $R^6$ and $R^7$ independently is hydrogen or $C_1$-$C_6$ alkyl;
$R^5$ is hydrogen or $C_1$-$C_6$ alkyl; or a pharmaceutically acceptable salt thereof; and wherein
a) when at the same time Y is naphthyl; $R^3$ is hydrogen, halogen, cyano or $C_1$-$C_6$ alkyl; $R^5$ is hydrogen; m is zero and n, R and $R^1$ are as defined above, then $R^4$ is other than hydrogen;
b) when at the same time Y is quinolyl or isoquinolyl; $R^3$ is hydrogen, halogen, cyano or $C_1$-$C_6$ alkyl; n is zero, 1 or 2; $R^5$ is hydrogen; m is zero and R and $R^1$ are as defined above, then $R^4$ is other than hydrogen; and
c) when at the same time Y is tetralyl in which only the benzene moiety is substituted, $R^3$ is hydrogen, halogen, cyano or $C_1$-$C_6$ alkyl; n is zero, 1 or 2; $R^5$ is hydrogen; m is zero, R is hydrogen and $R^1$ is as defined above, then $R^4$ is other than hydrogen; or a pharmaceutically acceptable salt thereof.

14. A method of treating a pathological proliferative disorder comprising administering to a patient a therapeutically effective amount of a compound of formula (I)

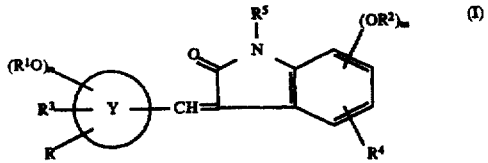

wherein
Y is a moiety selected from the group consisting of naphthyl, tetrayl, quinolyl and isoquinolyl;
R is hydrogen or an oxo (=O) group when Y is tetralin; or R is hydrogen when Y is naphthyl, quinolyl or isoquinolyl;
each of $R^1$ and $R^2$ independently is hydrogen, $C_1$-$C_6$ alkyl or $C_2$-$C_6$ alkanoyl;
m is zero, 1 or 2;
n is zero, 1, 2 or 3;
each of $R^3$ and $R^4$ independently is hydrogen, halogen, cyano, $C_1$-$C_6$ alkyl, carboxy, nitro or —$NR^6R^7$ in which each of $R^6$ and $R^7$ independently is hydrogen or $C_1$-$C_6$ alkyl;
$R^5$ is hydrogen or $C_1$-$C_6$ alkyl; or a pharmaceutically acceptable salt thereof; with the provisos that
a) when at the same time Y is naphthyl; $R^3$ is hydrogen, halogen, cyano or $C_1$-$C_6$ alkyl; $R^5$ is hydrogen; m is zero and n, R and $R^1$ are as defined above, then $R^4$ is other than hydrogen;
b) when at the same time Y is quinolyl or isoquinolyl; $R_3$ is hydrogen, halogen, cyano or $C_1$-$C_6$ alkyl; n is zero, 1 or 2; $R^5$ is hydrogen; m is zero and R and $R^1$ are as defined above, then $R^4$ is other than hydrogen; and
c) when at the same time Y is tetralyl in which only the benzene moiety is substituted, $R^3$ is hydrogen, halogen, cyano or $C_1$-$C_6$ alkyl; n is zero, 1 or 2; $R^5$ is hydrogen; m is zero, R is hydrogen and $R^1$ is as defined above, then $R^4$ is other than hydrogen.

15. A method of treating a pathological proliferative disorder comprising administering to a patient a therapeutically effective amount of a compound selected from the group consisting of
3-((8'-hydroxy-7'-quinolyl)methylene)-2-oxindole;
3-((5'-hydroxy-4'-quinolyl)methylene)-2-oxindole;
3-((8'-hydroxy-4'-quinolyl)methylene)-2-oxindole;
5-hydroxy-3-((5'-methoxy-3'-indolyl)methylene)-2-oxindole;
5-amino-3-((5'-methoxy-3'-indolyl)methylene)-2-oxindole;
5-hydroxy-3-((2'-methyl-3'-indolyl)methylene)-2-oxindole;
3-((2'-methyl-3'-indolyl)methylene)-2-oxindole;
3-((5'-cyano-3'-indolyl)methylene)-2-oxindole;
3-((5'-hydroxy-3'-indolyl)methylene)-2-oxindole;
3-((5'-methoxy-3'-indolyl)methylene)-2-oxindole;
or a pharmaceutically acceptable salt thereof.

16. A process for the preparation of a compound of formula (I) according to claim 1 or a pharmaceutically acceptable salt thereof, the process comprising condensing an aldehyde of formula (II)

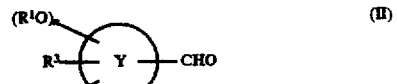

wherein Y, n, R, $R^1$ and $R^3$ are as defined in claim 1, with a compound of formula (III)

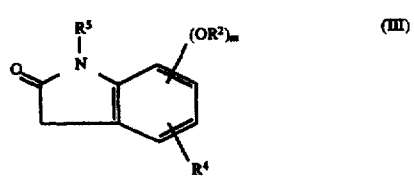

wherein, m, $R^2$, $R^4$ and $R^5$ are as defined in claim 1.

17. The process of claim 16, which further comprises: salifying a compound of formula (I) to form a pharmaceutically acceptable salt thereof.

18. The process of claim 16, which further comprises separating a mixture of isomers of a compound of formula (I) into single isomers.

* * * * *